United States Patent
Ingber et al.

(10) Patent No.: US 11,499,131 B2
(45) Date of Patent: Nov. 15, 2022

(54) SYSTEMS AND METHODS FOR CELL CULTURE DEVICE INTERCONNECTION AND FLUIDIC DEVICE INTERCONNECTION

(71) Applicant: PRESIDENT AND FELLOWS OF HARVARD COLLEGE, Cambridge, MA (US)

(72) Inventors: Donald E. Ingber, Boston, MA (US); Daniel Levner, Boston, MA (US); Guy Thompson, II, Watertown, MA (US); Jose Fernandez-Alcon, Cambridge, MA (US); Christopher David Hinojosa, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 16/593,646

(22) Filed: Oct. 4, 2019

(65) Prior Publication Data

US 2020/0277558 A1    Sep. 3, 2020

Related U.S. Application Data

(62) Division of application No. 14/904,640, filed as application No. PCT/US2014/046439 on Jul. 11, 2014, now Pat. No. 10,465,158.

(Continued)

(51) Int. Cl.
*C12M 1/00* (2006.01)
*C12M 3/06* (2006.01)
(Continued)

(52) U.S. Cl.
CPC ....... *C12M 29/10* (2013.01); *B01L 3/502715* (2013.01); *C12M 21/08* (2013.01);
(Continued)

(58) Field of Classification Search
CPC ........ B01L 2200/027; B01L 3/502715; C12M 29/10; C12M 29/00; C12M 21/08; C12M 23/16; C12M 41/00; C12M 41/48
See application file for complete search history.

(56) References Cited

U.S. PATENT DOCUMENTS

| 5,200,151 A | 4/1993 | Long |
| 7,275,562 B2 | 10/2007 | Barth et al. |

(Continued)

FOREIGN PATENT DOCUMENTS

| JP | 2009-148218 A | 7/2009 |
| JP | 2010-148384 A | 7/2010 |

(Continued)

*Primary Examiner* — Brian J. Sines
(74) *Attorney, Agent, or Firm* — Nixon Peabody LLP; David S. Resnick; David F. Crosby

(57) ABSTRACT

Systems and methods interconnect cell culture devices and/or fluidic devices by transferring discrete volumes of fluid between devices. A liquid-handling system collects a volume of fluid from at least one source device and deposits the fluid into at least one destination device. In some embodiments, a liquid-handling robot actuates the movement and operation of a fluid collection device in an automated manner to transfer the fluid between the at least one source device and the at least one destination device. In some cases, the at least one source device and the at least one destination device are cell culture devices. The at least one source device and the at least one destination device may be microfluidic or non-microfluidic devices. In some cases, the cell culture devices may be microfluidic cell culture devices. In further cases, the microfluidic cell culture devices may include organ-chips.

7 Claims, 13 Drawing Sheets

Related U.S. Application Data

(60) Provisional application No. 61/845,666, filed on Jul. 12, 2013.

(51) Int. Cl.
    *B01L 3/00*        (2006.01)
    *C12M 3/00*       (2006.01)
    *C12M 1/12*       (2006.01)
    *C12M 1/36*       (2006.01)
    *B01L 3/02*        (2006.01)

(52) U.S. Cl.
CPC ............ *C12M 23/16* (2013.01); *C12M 23/38* (2013.01); *C12M 23/58* (2013.01); *C12M 29/00* (2013.01); *C12M 29/20* (2013.01); *C12M 37/04* (2013.01); *C12M 41/48* (2013.01); *B01L 3/0293* (2013.01); *B01L 2200/027* (2013.01); *B01L 2300/0816* (2013.01)

(56) References Cited

U.S. PATENT DOCUMENTS

| | | |
|---|---|---|
| 2002/0131902 A1 | 9/2002 | Levy |
| 2004/0262162 A1 | 12/2004 | Roach et al. |
| 2008/0194012 A1 | 8/2008 | Lee et al. |
| 2009/0023608 A1* | 1/2009 | Hung ................ B01L 3/502715 506/32 |
| 2009/0203126 A1 | 8/2009 | Hung et al. |
| 2010/0291584 A1 | 11/2010 | Tseng et al. |
| 2011/0250585 A1 | 10/2011 | Ingber et al. |
| 2011/0269121 A1 | 11/2011 | Gaitas et al. |
| 2011/0296931 A1 | 12/2011 | Warhurst et al. |
| 2012/0003732 A1 | 1/2012 | Hung et al. |
| 2013/0017127 A1 | 1/2013 | Tokmaru |
| 2013/0090268 A1 | 4/2013 | Hung et al. |
| 2013/0171679 A1 | 7/2013 | Lee et al. |
| 2014/0099705 A1 | 4/2014 | Hung et al. |
| 2014/0186414 A1 | 7/2014 | Ingber et al. |
| 2014/0220617 A1 | 8/2014 | Yung et al. |
| 2014/0342445 A1 | 11/2014 | Ingber et al. |
| 2015/0004077 A1 | 1/2015 | Wikswo et al. |
| 2015/0209783 A1 | 7/2015 | Ingber et al. |

FOREIGN PATENT DOCUMENTS

| | | |
|---|---|---|
| JP | 2010-148457 A | 7/2010 |
| WO | 2009/006422 A1 | 1/2009 |
| WO | 2010/009307 A2 | 1/2010 |
| WO | 2010/123594 A2 | 10/2010 |
| WO | 2012/118799 A2 | 9/2012 |
| WO | 2013/086486 A1 | 6/2013 |

* cited by examiner

SYSTEMS AND METHODS FOR CELL CULTURE DEVICE INTERCONNECTION AND FLUIDIC DEVICE INTERCONNECTION

CROSS-REFERENCE TO RELATED APPLICATIONS

This application is a divisional under 35 U.S.C. § 121 of co-pending U.S. application Ser. No. 14/904,640, filed Jan. 12, 2016, which is a 35 U.S.C. § 371 National Phase Entry of International Application No. PCT/US2014/046439 filed Jul. 11, 2014, which designates the U.S., and which claims benefit under 35 U.S.C. § 119(e) of U.S. Provisional Application No. 61/845,666 filed Jul. 12, 2013, the contents of which are incorporated entirely herein by reference.

STATEMENT REGARDING FEDERALLY SPONSORED RESEARCH

This invention was made with government support under grant no. W911NF-12-2-0036 awarded by U.S. Department of Defense, Defense Advanced Research Projects Agency. The government has certain rights in the invention.

BACKGROUND

Technical Field of the Invention

The present invention relates to cell culture devices and fluidic devices. More specifically, the present invention relates to systems and methods that interconnect cell culture devices and/or fluidic devices by transferring discrete volumes of fluid between devices.

Description of the Prior Art

According to existing approaches, fluidic (microfluidic and/or non-microfluidic) devices are typically interconnected using tubing and valves that connect the output of one device to the input of another. However, the use of tubing and valves presents some disadvantages.

In existing systems, a significant length of tubing is needed to connect two devices, and as such, the tubing may end up with a large quantity of dead volume that cannot be used by the devices. At most, this type of interconnection is effective only where small volumes of fluid need to be transferred between devices. Disadvantageously, the tubing must typically be primed with fluid in a complex and time-consuming set of operations that wastes fluid. Furthermore, after a procedure is completed (e.g., between experiments), the connective tubing must be flushed in another complex set of operations. Alternatively, a large quantity of tubing must be wastefully discarded and replaced before a subsequent procedure can be conducted.

While connecting a small number of devices may be possible with existing systems, it becomes increasingly difficult and complex to connect greater numbers of devices. This is especially the case when the interconnection system must use valves to allow the interconnection system to be configured or modified. More devices require more tubing and valves adding to the complexity and the expense of the system. For example, commercial low-volume selector valves used in such systems are very expensive. In addition, future undefined experiments may require new valve designs and tubing architectures. In general, existing approaches do not scale well for interconnection systems that require multiple replicates that need to be similarly interconnected.

The use of tubing for interconnection also results in a system where chemical signals from the devices may be physically separated at a relatively large distance and may take longer times to travel through the tubing and to arrive at the destination. In devices that are connected in series, with a pump pushing liquid from one end, the fluid pressure in the first device will be significantly higher than in the last device. If pumps are connected between devices to alleviate the aforementioned pressure drop then even small mismatches in the pump flow rates and/or pressure will lead to a volume accumulation and pressure increases that may need to be corrected through pressure relief valves and overflow/supplement reservoirs.

Accordingly, there is a need for an improved system for interconnecting fluidic (microfluidic and/or non-microfluidic) devices.

SUMMARY

Aspects of the present invention relate to systems and methods that interconnect cell culture devices and/or fluidic devices by transferring discrete volumes of fluid between devices. In particular, aspects of the present invention provide a liquid-handling system that collects a volume of fluid from at least one source device and deposits the fluid into at least one destination device. In some embodiments, a liquid-handling robot actuates the movement and operation of a fluid collection device in an automated manner to transfer the fluid between the at least one source device and the at least one destination device. Advantageously, aspects of the present invention achieve effective fluid transfer between devices without requiring a complex configuration of tubing and valves. Furthermore, aspects of the present invention provide a wider range of interconnection configurations and architectures, and simplify the process for making changes to the interconnection configurations and architectures.

According to an example embodiment, a system facilitates biological communication between two or more cell culture devices. The system includes at least one fluid collection device configured to collect a first fluid from one or more first cell culture devices and to deposit a second fluid into one or more second cell culture devices. The system includes a movement system configured to be coupled to the at least one fluid collection device and to move the at least one fluid collection device into a desired position relative to at least one selected first cell culture device or at least one selected second cell culture device. When the at least one fluid collection device positioned in the desired position relative to the at least one selected first cell culture device, the at least one fluid collection device collects respective first fluid from the at least one selected first cell culture device. When the at least one fluid collection device is positioned in the desired position relative to the at least one selected second cell culture device, the at least one fluid collection device deposits respective second fluid into the at least one selected second cell culture device.

In some cases, the at least one selected first cell culture device or at least one selected second cell culture device may include at least one microfluidic cell culture device. In further cases, the at least one microfluidic cell culture device may include at least one fluid channel with at least one dimension that is less than or equal to approximately 3 mm. In yet further cases, the at least one microfluidic cell culture device may include an organ-chip.

Correspondingly, a method transfers fluid from a first cell culture device to a second cell culture device. The method includes moving a fluid collection device to a first desired position relative to the first cell culture device; collecting a first fluid from the first cell culture device; moving the fluid collection device to a second desired position relative to the second cell culture device; and depositing a second fluid into the second cell culture device, wherein the second fluid includes at least a portion of the first fluid collected from the first cell culture device.

These and other capabilities of the invention, along with the invention itself, will be more fully understood after a review of the following figures, detailed description, and claims.

Figure 1:
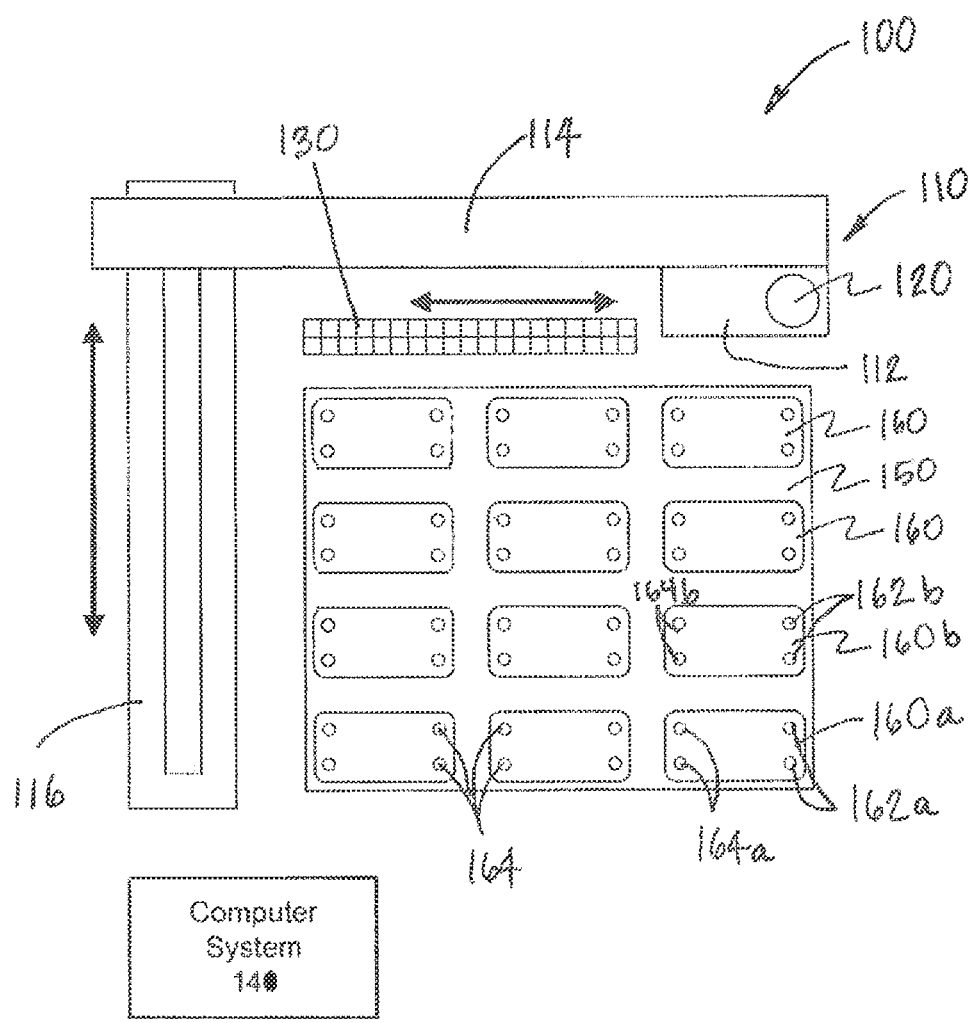
FIG. 1 illustrates an example interconnection system for a plurality of fluidic devices according to aspects of the present invention.

The accompanying drawings, which are incorporated into this specification, illustrate one or more exemplary embodiments of the inventions and, together with the detailed description, serve to explain the principles and applications of these inventions. The drawings and detailed description are illustrative, not limiting, and can be adapted without departing from the spirit and scope of the inventions.

DETAILED DESCRIPTION

Aspects of the present invention relate to systems and methods that interconnect cell culture devices and/or fluidic devices by transferring discrete volumes of fluid between devices. In particular, aspects of the present invention provide a liquid-handling system that collects a volume of fluid from at least one source device and deposits the fluid into at least one destination device. In some embodiments, a liquid-handling robot actuates the movement and operation of a fluid collection device in an automated manner to transfer the fluid between the at least one source device and the at least one destination device. Advantageously, aspects of the present invention achieve effective fluid transfer between devices without requiring a complex configuration of tubing and valves. Furthermore, aspects of the present invention provide a wider range of interconnection configurations and architectures, and simplify the process for making changes to the interconnection configurations and architectures.

In one embodiment, the at least one source device and the at least one destination device are cell culture devices. According to aspects of the present invention, the at least one source device and the at least one destination device may be microfluidic or non-microfluidic devices. Thus, in some cases, the cell culture devices may be tissue culture wells, culture plate inserts (e.g., CORNING® TRANSWELL®), or the like. Meanwhile, in other cases, the cell culture devices may be microfluidic cell culture devices (e.g., having at least one fluid channel (see, e.g., input or output channel 662 of FIG. 6) having at least one dimension that is less than or equal to approximately 3 mm).

A further embodiment interconnects cell culture devices that are each used to mimic at least one aspect, e.g., a physiological function, of a respective biological cell system. Thus, the interconnected cell culture devices can simulate the interaction between cell systems to facilitate the study of multi-cell, multi-tissue, or multi-organ response. In particular, the movement of liquid between cell culture devices simulates the communication of biochemical signals or other biological product from one cell system to another. In one approach, a liquid-handling robot links the cell culture devices to other cell culture devices just as cell systems in the body are linked by vasculature or other biological connection. Therefore, aspects of the present invention allow the interactions between organs, tissues, or cell types to be studied using a collection of cell culture devices (e.g., microfluidic devices, tissue culture wells, culture plate inserts, and/or combinations thereof). For example, an inflammatory response in a first organ can cause a response in a second organ, which in turn may affect a biological function of the second organ or how the second organ responds to a drug. Aspects of the present invention allow one to simulate and study ex vivo the response of the second organ to such stimulus which may occur in vivo. Microfluidic devices that are used to mimic aspects of a biological cell system, e.g., a tissue type or organ, are also referred to organs-on-chips or organ-chips as described further below. The interconnected cell culture devices may further include traditional tissue culture, 3D cultures, culture plate devices, co-cultures, organoids, surface-patterned cultures, clinical biopsies or samples, primary tissue, and/or harvested cells (including gametocytes), and/or combinations thereof.

Figure 2:
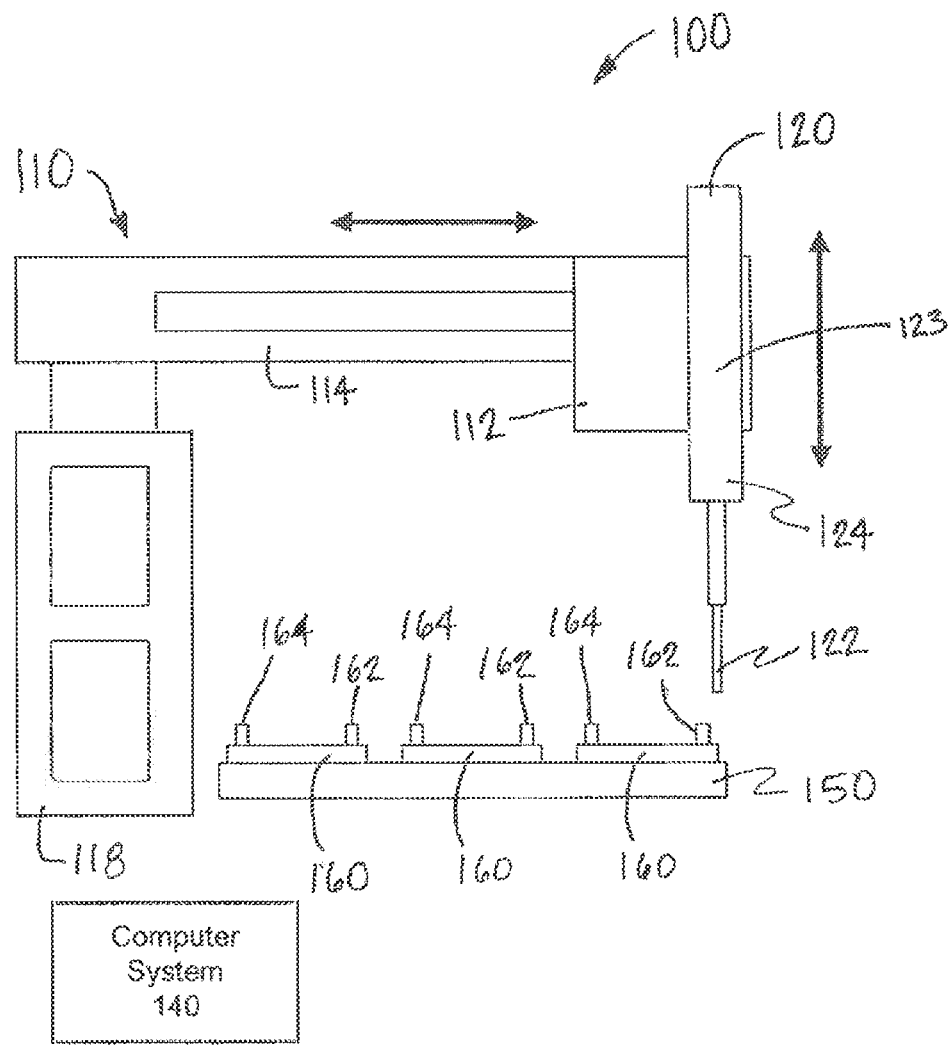
FIG. 2 illustrates another view of the example interconnection system of FIG. 1.

Referring to FIGS. 1 and 2, an interconnection system 100 according to aspects of the present invention is illustrated. The interconnection system 100 includes a movement system 110, a fluid collection device 120, and one or more fluidic devices 160 arranged on a platform 150. As used herein, fluidic devices include devices with at least one fluid and are not limited to devices with at least one fluidic conduit. As such, the fluidic devices 160 may include cell culture devices (e.g., microfluidic devices, tissue culture wells, culture plate inserts, 3D cultures, and/or combinations thereof). In addition, the fluidic devices 160 may be microfluidic and/or non-microfluidic. Moreover, the fluidic devices 160 may be microfluidic cell culture devices (e.g., having at least one fluid channel having at least one dimension that is less than or equal to approximately 3 mm). As shown in FIGS. 1 and 2, each fluidic device 160 includes at least one output port 162 though which fluid can be collected from the fluidic device and at least one input port 164 through which fluid can be deposited into the fluidic devices 160. As described further below, any of the output ports 162 or input ports 164 may include a chamber (sometimes also referred to as a reservoir) that can retain the fluid to be collected from or deposited into the respective port.

Figure 13:
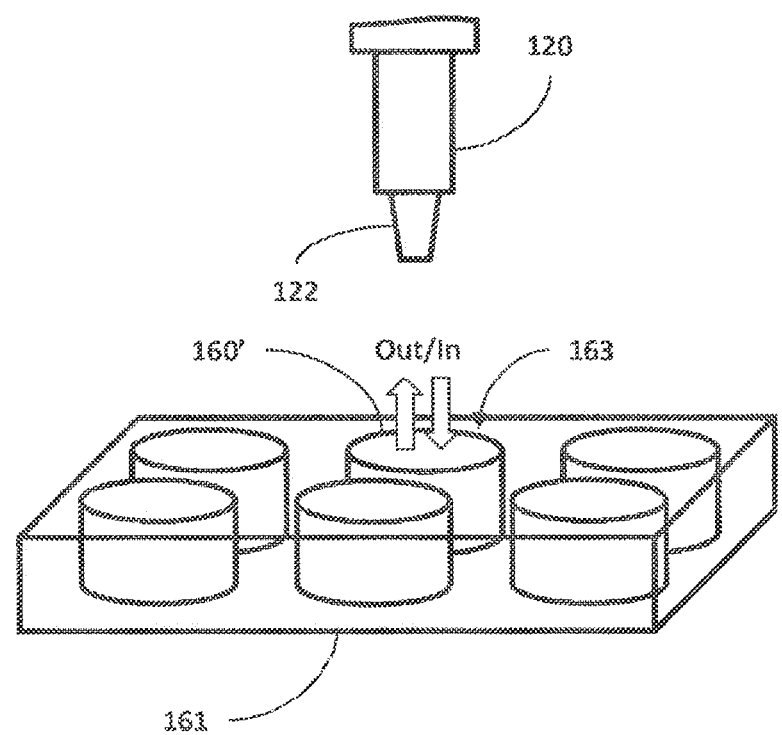
FIG. 13 illustrates an example fluidic device according to aspects of the present invention.

Instead of only employing ports dedicated to either output or input, the fluidic devices described herein may employ any port, opening, access, etc., for both output and input of fluid. As shown in FIG. 13, for example, a fluidic device 160' includes a cell culture well (e.g., in a multi-well device 161), where the fluid is collected and deposited through a common opening 163 at the top of the fluidic device 160', i.e., the opening 161 serves as both an output and an input. Thus, it is contemplated that the description of output ports and input ports may refer to common output/input port(s).

Referring again to FIGS. 1 and 2, the movement system 110 can move the fluid collection device 120 according to one or more degrees of freedom to one or more source fluidic devices 160a where the fluid collection device 120 can collect an amount of fluid from each source fluidic device 160a via respective output ports 162a. The movement system 110 can then move the fluid collection device 120 to one or more destination fluidic devices 160b where the fluid collection device 120 can deposit, via respective input ports 164b, some of the fluid collected from the source fluidic devices 160a. The movement system 110 can thus be employed to transfer fluid between any of the fluidic devices 160 with the fluid collection device 120. In this way, the system 100 interconnects the fluidic devices 160, e.g., to simulate interconnection between cell systems.

The system 100 can be used to implement a variety of interconnection topologies. For example, the system 100 may be configured to interconnect one or more fluidic devices 160 in series, in parallel or in combination thereof, as well as effectively include recirculation around one or more fluidic devices 160. The system can be adapted to modify the interconnection topology during operation.

Furthermore, applying aspects of the present invention, the fluidic devices 160 are perfused with the fluid deposited into the at least one input port 164 of the fluidic devices 160. In particular, the system 100 or one or more fluidic devices 160 can include one or more perfusion mechanisms, e.g., pumps. The perfusion mechanisms perfuse one or more fluidic devices 160 with fluid deposited through their respective input port(s) 164 and corresponding chamber(s). Without being bound by theory, during perfusion of fluidic devices, the fluid collection device 120 is no longer occupied and is free to continue fluidic transfers.

Any number of portions of the fluid from the source fluidic device 160a can be distributed to any number of destination fluidic devices 160b. Additionally or alternatively, the collected fluid can be deposited into other types of destination devices (other than destination fluidic devices 160b). Other types of destination devices include, for example, a destination reservoir for storing the fluid or an instrument for analyzing the fluid. Additionally or alternatively, some of the collected fluid can be deposited back into the source fluidic device 160a.

Fluid may be collected from more than one source fluidic devices 160a before being deposited in the destination fluidic device(s) 160b. Additionally or alternatively, fluid may be collected from other types of source devices (other than fluidic devices 160), such as a source reservoir.

In general, the fluid collection device 120 can collect fluid from one or more source fluidic devices 160a and optionally one or more source reservoirs and deposit portions of the collected fluid into one or more destination fluidic devices 160b and optionally one or more destination reservoirs or analysis instruments.

In some cases, the collected fluid from the source device(s) can be processed before being deposited into the destination device(s). For example, the fluid collected from a source fluidic device 160a may be mixed or combined with additives from a source reservoir. For instance, such additives may include drugs, test compounds, biochemical signals, proteins, small molecules, hormones, nutrients, antibodies, cells (including immune cells), toxins, pathogens, marker components, or anti-coagulants. Additionally or alternatively, the collected fluid may be processed to change one or more physical or chemical characteristics, such as concentration, temperature, pressure, absorbed gases, pH or chemical content. Additionally or alternatively, the collected fluid may be filtered.

According to aspects of the present invention, the movement system 110 may employ mechanical systems (e.g., linkages), fluid systems (e.g., hydraulics, pneumatics, etc.), and/or other mechanical or electromechanical systems to actuate and control movement of the fluid collection device 120. According to aspects of the present invention, the movement system 110 may include robotically controlled elements that electromechanically move the fluid collection device 120 between locations. In such cases, the interconnection system 100 provides a fluid-handling robot. An example of robotically controlled elements can be found in the Tecan Cavro Omni Robot available from Tecan Group, Ltd. (Mannedorf Switzerland).

As shown in shown in FIGS. 1 and 2, the movement system 110 may include a z-axis actuator 112, an x-axis actuator 114, and a y-axis actuator 116 that are coupled to and move the fluid collection device 120 linearly along three axes. In general, however, the movement system 110 can include any number of actuators that can move the fluid collection device 120 to a desired location according to any degrees of freedom. The actuators may include any combination of linear actuators that move along an axis and/or rotary actuators that move about an axis.

In some embodiments, the system 100 may employ more than one fluid collection devices 120, which can be actuated using one or more movement systems 110. In some cases, the fluid collection devices 120 may be mechanically coupled along one or more degrees of motion (e.g., having common x- and y-axis but independent z-axes). Additionally or alternatively, the multiple fluid collection devices 120 may be moved independently through at least partially overlapping ranges of motion.

A computer system 140 is coupled to and controls the actuators 112, 114, 116. In particular, the computer system 140 can control the x-axis actuator 114 and the y-axis actuator 116 to position the fluid collection device 120 along an x-y plane over the fluidic devices 160 and over the at least one output ports 162 and the at least one input ports 164 of a selected fluidic device 160. The movement system 110 may be mounted on one or more supports or a stand 118 to allow the movement system 110 to move the fluid collection device 120 easily over the x-y plane without inadvertently contacting the fluidic devices 160. The computer system 140 can then control the z-axis actuator 112 to lower the fluid collection device 120 to engage the at least one output ports 162 and the at least one input ports 164 of the selected fluidic device 160 to collect or deposit fluid.

The computer system 140 may include one or more processors of any architecture (e.g. x86, x86-64, ARM, Power, AVR, PIC, MSP430, etc.) and associated memory (e.g. RAM, ROM, magnetic, optical and solid state media, etc.) that stores programs with instructions that can be read and executed by one or more of the processors. The computer system 140 may also include a display and input devices (e.g., a keyboard and mouse) to enable a user to interact and control the operation of the computer system 140 and the movement system 110. The computer system 140 may be connected to the movement system 110 using a wired (e.g., RS-232, RS-485, USB, FireWire, Ethernet, I2C) or wireless (e.g., Bluetooth, WiFi, ZigBee) connection. The computer 140 may also include software that enables the user to interact and control the operation of the computer system remotely.

In operation, the interconnection system 100 can be programmed with the positions of each fluidic device 160 and its respective output port(s) 162 and input port(s) 164. The computer system 140 can then use these programmed positions to cause the movement system 110 to move the fluid collection device 120 accurately into position to engage the output port(s) 162 or the input port(s) 164. For example, an operator can define a protocol for transferring fluids between selected fluidic devices 160 with the movement system 110 and the fluid collection device 120. The protocol defines a set of programmed actions to be initiated in a defined sequence by the computer system 140. The program can specify the volume of fluid to be transferred as well as the timing of the transfer for each step. The timing can be specified as an absolute time measured from a defined reference time or time relative to a prior action. The computer system 140 may employ scheduling software that allows the predefined set of actions to be executed based on a schedule. When necessary, the scheduling software can resolve scheduling conflicts, for example, between scheduled transfer of fluid between fluidic devices 160 and regularly scheduled collection of samples that are stored for later analysis. In addition, the schedule may be modifiable by a user during its execution. The scheduled transfer of fluid can, for example, include scheduled transfers every 1 min, 2 min, 5 min, 10 min, 15 min, 30 min, 1 hour, 2 hour, 6 hour, 12 hour, 24 hour, 36 hour for some duration of time, and/or include aperiodic transfer on an as-needed basis. However, it understood that the transfers can be scheduled according to any time protocol.

As described above, a portion of collected fluid can be deposited into an analysis instrument to analyze the fluid. The analysis instrument, for example, can involve mass spectrometry, ELISA and other analytic biochemistry assays, electrochemical sensors, thermal sensors, optical sensors (including surface-Plasmon sensors, various optical resonators, waveguide sensors, fluorescence reader, optical-density readers), bead-based sensors, flow cytometers, various array-binding assays (including gene chips and proteomic chips), etc. In some cases, an analysis of the collected fluid can determine the next action in a protocol. For example, the system 100 might not transfer the output of one fluidic device 160 to another fluidic device until characteristics of the collected fluid meets particular criteria according to the analysis instrument. The analysis may involve any physical, chemical, or biochemical characteristics of the fluid, such as, temperature, viscosity, pH, osmolarity, osmolality, salinity, glucose concentration, hormone level, lipid concentration, drug concentration, oxygen or other gas concentration, etc.

For example, the instrument can measure the pH of a sample of the collected fluid, and based on the measurement, the computer system 140 can initiate an action that adds fluid from a first source reservoir if the pH needs to raised or adds fluid from a second source reservoir if the pH needs to be lowered. The pH adjusted fluid can then be deposited in the destination device(s) or stored for later use.

In another example, the instrument can measure the osmolarity or osmolality of a sample of the collected fluid, and based on the measurement, the computer system 140 can initiate an action to add fluid from a storage reservoir, e.g., containing deionized water, if the osmolarity or osmolality needs to be lowered. Such action can be used to compensate for fluid evaporation during a process.

In other cases, the analysis of a sample of collected fluid sample can be used to modify the protocol for future procedures. For example, a stimulus may be introduced to a fluidic device 160 to produce a change in the characteristics of the fluid in the fluidic device 160 and of any fluid subsequently collected via the corresponding output port 162. However, if an analysis of the fluid in the fluidic device 160 indicates that the intended change in character has not been achieved, the protocol may be modified to increase or decrease the stimulus in future procedures so that the desired change in character of the fluid is indeed achieved.

Additionally or alternatively, the movement system 110 can include an embedded control system that stores a predefined program that the movement system 110 can follow without requiring the movement system 110 to communicate with the computer system 140. The embedded control system can include one or more processors of any architecture (e.g., x86, x86-64, ARM, Power, AVR, PIC, MSP430, etc.) and associated memory (e.g. RAM, ROM, magnetic, optical and solid state media, etc.) that stores programs with instructions that can be read and executed by one or more of the processors. In some cases, the embedded control system can communicate with the computer system 140 to receive information and/or program data that can be stored in memory of the embedded control system. The embedded control system can then either automatically or upon user initiated instruction (e.g., pressing a button or operating switch) initiate the execution of a predefined program that involves transfer of fluid between the fluidic devices 160 and/or other source/destination devices.

In general, the fluid collection device 120 can employ any device that allows it to be directly or indirectly coupled to the fluidic devices 160 in order to draw or deposit fluid, e.g., via the output ports 162 and input ports 164. As shown in FIGS. 1 and 2, the fluid collection device 120 includes a tip 122 that can engage the ports 162, 164 of the fluidic devices 160 to collect fluid from or deposit fluid into the fluidic devices 160. The tip 122 of the fluid collection device 120 may also be combined with a collection chamber 123 in which the fluid can be stored after collection and from which the fluid can be expelled for depositing into destination devices. The tip 122 may be replaced at any time during operation, potentially through the automatic action of the instrument. Additionally, the system 100 may include a tip-wash apparatus that can clean and/or sterilize a tip 122 before, after, and/or between uses.

The fluid collection device 120 is also coupled to one or more sources of positive and negative pressure that allow fluid to be correspondingly drawn into or expelled from the tip 122. The pressure may be applied directly to the fluid or through a working fluid that may include one or more liquid volumes, gas volumes, and/or combinations thereof. One or more valves may be employed to control the application of the positive or negative pressure. Additionally, the fluid collection device 120 may also include sensors, e.g., resistive, capacitive or pressure sensors, that detect the volume of fluid drawn or expelled. The source(s) of positive and negative pressure may be external to the fluid collection device 120 or may reside internally in a housing 124 of the fluid collection device 120. For example, the housing 124 may include a pump, e.g., a motor driven piston, that controls the pressure within the tip 122. In some cases, the pump and other aspects of the fluid collection device 120 may also be coupled to and controlled by the computer system 140. The fluid collection device may also contain additional mechanisms, e.g., pumps and valves, that allow one or more cleaning fluids to be flushed through and/or around the tip 122 between transfers/procedures. In some embodiments, a wash station can be provided to permit washing the inside and/or outside the tip 122.

Accordingly, the fluid collection device 120 is configured to transfer any desired volume of fluid between any number of source devices and any number of destination devices. As such, the interconnection system 100, for example, can transfer volumes of 1 microliter, 2 microliters, 3 microliters, 4 microliters, 5 microliters, 10 microliters, 20 microliters, 30 microliters, 40 microliters, 50 microliters, and volumes up to 5 milliliters. These and other volumes can be transferred by making one or more trips between the source device(s) and the destination device(s).

In some embodiments, the fluid collection device 120 may include one or more pipettes. Examples of pipettes that can be employed according to aspects of the present invention include an air displacement pipette (Cavro ADP, Tecan Group, Ltd. (Mannedorf Switzerland)) and an 8-channel pipetting head (Tecan Cavro, Tecan Group, Ltd., Mannedorf Switzerland).

In other embodiments, the fluid collection device 120 may include a spiraled or coiled microfluidic sampling device that allows the fluid collection device 120 to handle small volumes of fluid. An example of a spiraled or coiled microfluidic sampling device is disclosed in U.S. Pat. No. 7,275,562, which is hereby incorporated entirely herein by reference.

According to aspects of the present invention, the interconnection system 100 can include two or more fluid collection devices 120 to collect fluid from two or more source devices or deposit fluid into two or more destination devices at substantially the same time. In some embodiments, the tips 122 of the fluid collection devices 120 are spaced according to the spacing of the fluidic devices 160 as well as the output ports 162 and the input ports 164 of the fluidic devices 160. In some cases, it may be desirable to perform fluid transfer operations on two or more sets of fluidic devices 160 in the same or substantially similar ways. In one example, a plurality of microfluidic devices 160 are arranged in rows and columns and a plurality of fluid collection devices 120 are spaced apart according to the spacing of rows or columns to allow for simultaneous fluid transfer operations across columns or rows, respectively. As such, the same or similar processes can be more easily replicated across a plurality of fluidic devices 160.

Figure 12:
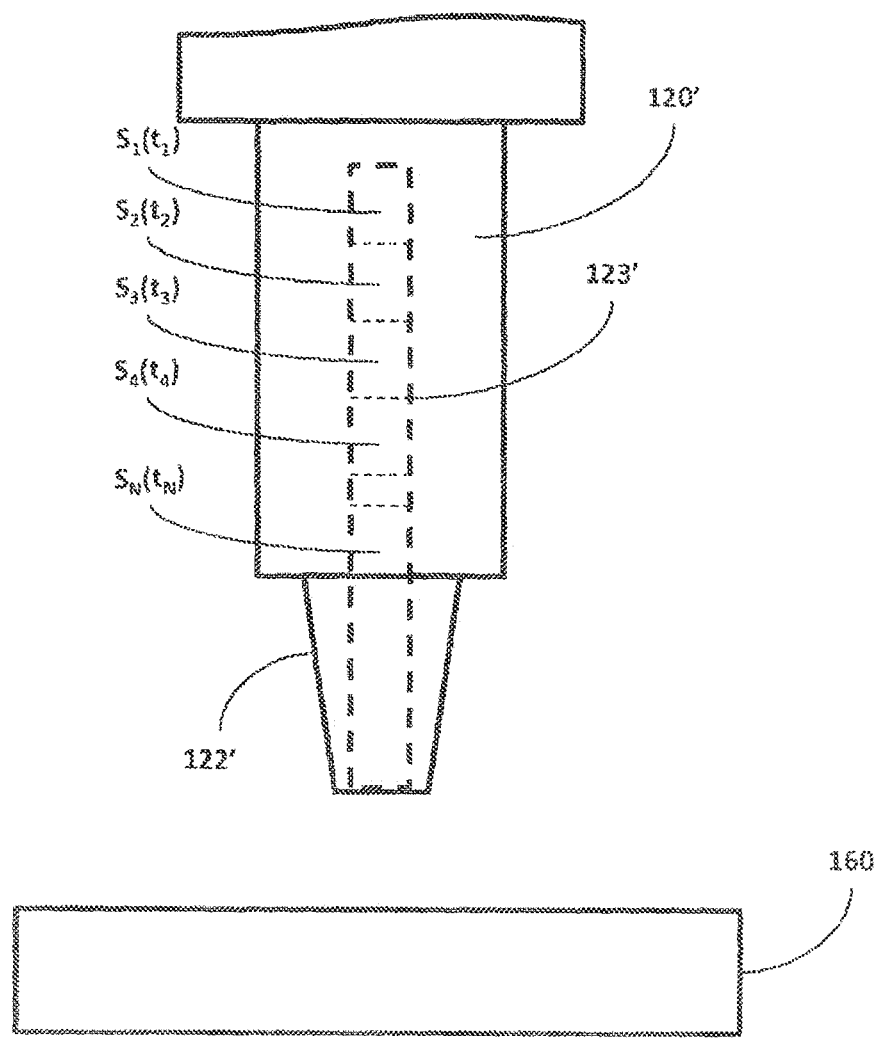
FIG. 12 illustrates an example collection chamber that retains time-based information according to aspects of the present invention.

Referring to FIG. 12, embodiments according to the present specification may be configured to retain time-based information associated with a series of fluid samples that are collected over a period of time. As shown in FIG. 12, a collection chamber 123' of a fluid collection device 120' is an elongated chamber that effectively allows a time-course of samples to be retained by limiting the diffusion or mixing of samples within the elongated chamber. Without being bound by theory, a sample collected within the collection chamber 123' can be viewed as effectively forming a series of fluid samples $S_1, S_2, S_3, S_4, \ldots, S_N$ to be collected via the tip 122' corresponding to times $t_1, t_2, t_3, t_4, \ldots, t_N$ from fluid in a fluidic device 160. In some embodiments, the fluid collection device 120' is continuously coupled to the fluidic device 160 while collecting the fluid samples $S_1, S_2, S_3, S_4, \ldots, S_N$ at the particular times, and as such, the movement system 110 does not need to move the fluid collection device 120'. The collection chamber 123' may be a microfluidic or capillary channel that receives the effective series of fluid samples $S_1, S_2, S_3, S_4, \ldots, S_N$, but minimizes the diffusion within the collection chamber 123' and mixing of the fluid samples $S_1, S_2, S_3, S_4, \ldots, S_N$. As such, each sample in the effective series of fluid samples $S_1, S_2, S_3, S_4, \ldots, S_N$ in the collection chamber 123' substantially retains the time-wise characteristics it had at the time of collection. The fluid in the fluidic device 160' may change over a period of time. For example, the concentration of one or more of constituent components, pH level, or bacteria concentration in the fluid of the fluidic device 160' can change over time. Each sample in the effective series of fluid samples $S_1, S_2, S_3, S_4, \ldots, S_N$ collected over the same period of time can substantially provide a respective snapshot of the changing characteristics of the fluid in the fluidic device 160'. The position of the sample along the collection chamber 123' indicates the relative time of collection $t_1, t_2, t_3, t_4, \ldots, t_N$. Accordingly, the fluid samples $S_1, S_2, S_3, S_4, \ldots, S_N$ provide the characteristics of the fluid in the fluidic device 160' as a function of time.

The effective series of fluid samples $S_1, S_2, S_3, S_4, \ldots, S_N$ in the collection chamber 123' can be transferred to another fluidic device (e.g., cell culture device, microfluidic or non-fluidic device, etc.), an elongated collection chamber, or an instrument for analysis (including time-based analysis). The effective series of fluid samples $S_1, S_2, S_3, S_4, \ldots, S_N$ in the collection chamber 123' may be deposited into another fluidic device at the rate it was collected from the fluidic device 160' to reproduce the rate of change of the characteristics originally experienced by the fluidic device 160'. Alternatively, effective series of fluid samples $S_1, S_2, S_3, S_4, \ldots, S_N$ in the collection chamber 123' may be deposited into another fluidic device at a rate slower or faster than the collection rate. The slower or faster rate allows one to study the impact of different rates of change of fluid characteristics. In other embodiments, the effective series of fluid samples $S_1, S_2, S_3, S_4, \ldots, S_N$ can be transferred to another elongated collection chamber from which it is delivered at a controlled rate to a cell-culture or analysis device. Accordingly, the transfer rate can be decoupled from the rate at which the samples are collected, which can enable the interconnection system to operate rapidly while maintaining the time-course of the effective series of fluid samples. In some embodiments, the tip 122 may comprise an elongated collection chamber so that an effective series of samples $S_1, S_2, S_3, S_4, \ldots, S_N$ may be maintained while the sample resides in the fluid collection device 120. The lateral dimensions of any of the said elongated collection chambers can be chosen to sufficient limit the diffusion and mixing of the sample therein.

According to aspects of the present invention, the interconnection system 100 may allow the tips 122 (including, when required, corresponding collection chambers/reservoirs 123) to be banked. In other words, the tips 122 can be reused for a designated purpose up until a designated expiration. As shown in FIG. 1, for example, the interconnection system 100 also includes one or more storage components 130 that allow the tips 122 of the fluid collection device 120 to be stored and tracked for later use. The tips 122 of the fluid collection device 120 can be automatically removed from the fluid collection device 120, stored in the storage components 130, and then later re-installed. In some cases, the interconnection system 100 can store and reuse the tips 122 that are used to collect fluid from a specific set of fluidic devices 160, and each tip is always used with a designated fluidic device 160 to prevent cross-contamination. For example, a first tip 122 is used to collect fluid from an output port 162 on a first fluidic device 160 and to deposit the fluid at the input port 164 of a second fluidic device 160. Prior to the next fluid transfer operation, the first tip 122 is removed and stored in a predefined bin location of the storage component 130 and a second tip 122 is used to transfer fluid from the second fluidic device 160 to a third fluidic device 160. The second tip 122 can be a new (clean) tip 122 or another designated reused tip 122 taken from another predefined bin of the storage component 130. The next operation that requires the transfer of fluid from the first fluidic device 160 to the second fluidic device 160 can be performed by first removing and storing the second tip 122 in its predefined bin in the storage component 130 and re-installing the first tip 122 prior to transferring fluids between the two devices. The tips 122 may be reused until they reach an expiration defined by the total number of uses, by an expiration date, and/or other appropriate criteria.

Figure 3:
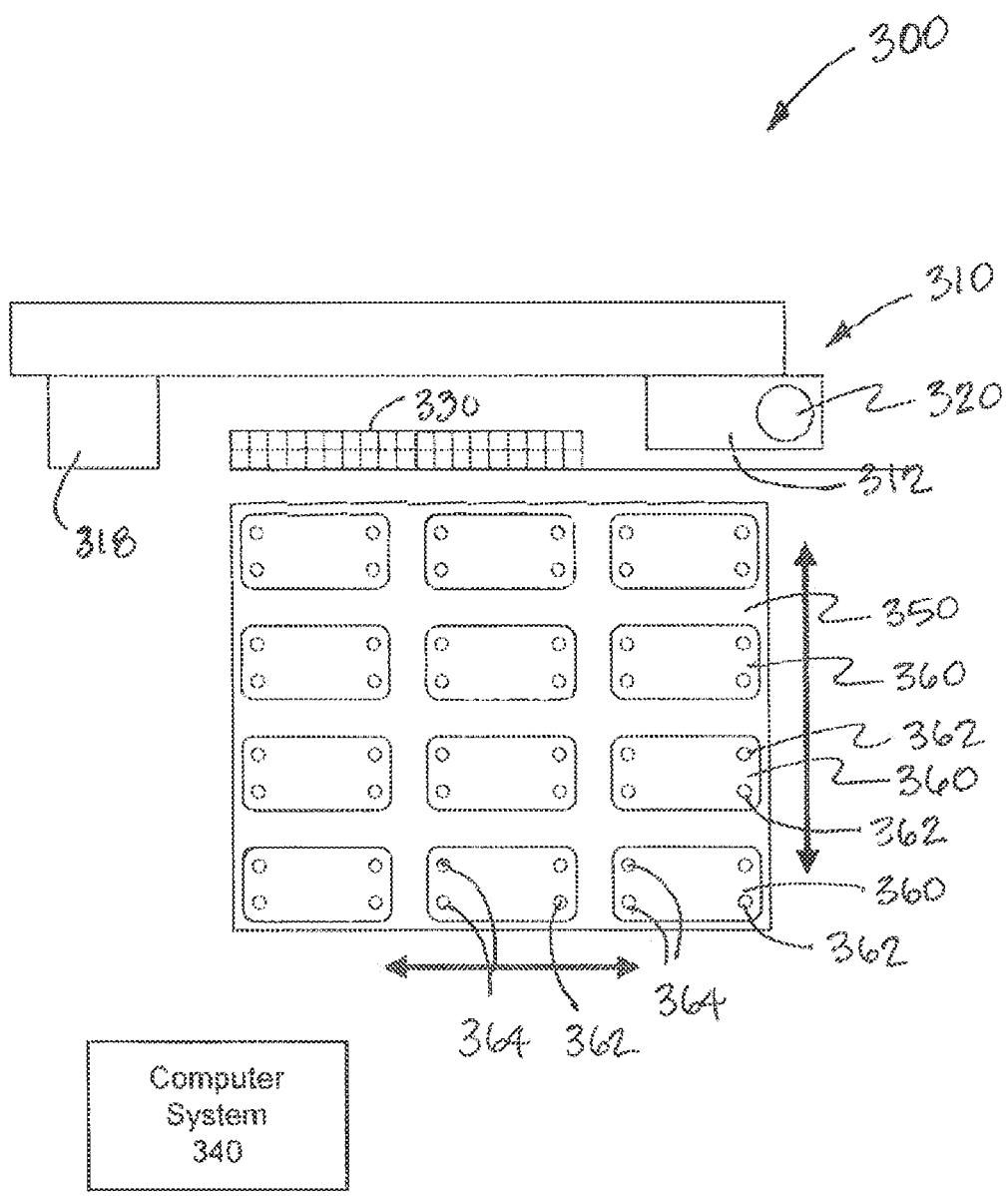
FIG. 3 illustrates another example interconnection system for a plurality of fluidic devices according to aspects of the present invention.
Figure 4:
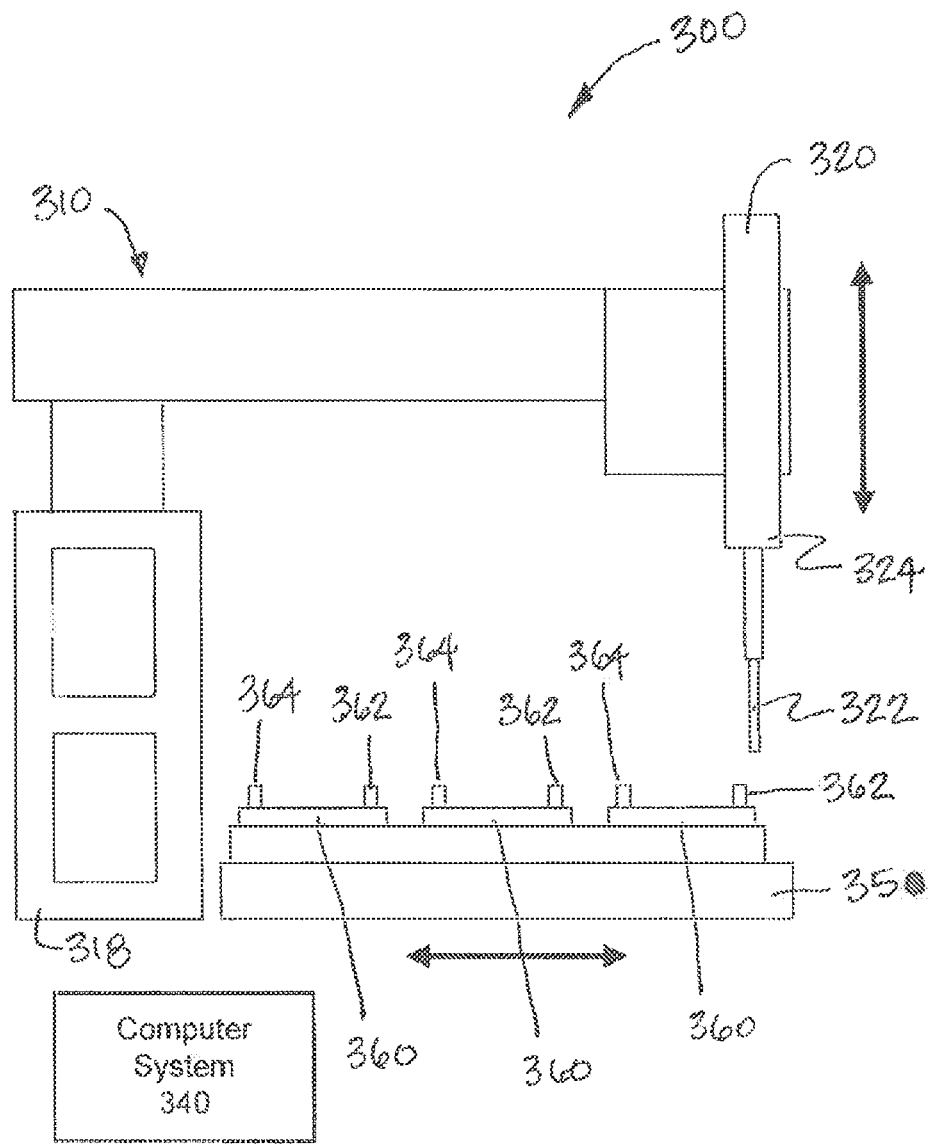
FIG. 4 illustrates another view of the example interconnection system of FIG. 3.

Referring to FIGS. 3 and 4, another example interconnection system 300 according to examples of the present invention is illustrated. The system 300 is similar in many aspects to the system 100 shown in FIGS. 1 and 2. The system 300 includes a movement system 310, a fluid collection device 320, and one or more fluidic devices 360 arranged on a platform 350. A computer system 340 controls aspects of the system 300. The fluidic devices 360 may be fluidic and/or microfluidic. Each fluidic device 360 includes at least one output port 362 though which fluid can be collected from the fluidic device 360 and at least one input port 364 through which fluid can be deposited into the fluidic device 360. The fluid collection device 320 includes a tip 322 that engages an output port 362 or an input port 364 of a selected fluidic device 360 to collect or deposit fluid, respectively. The movement system 310 causes relative movement between the fluid collection device 320 and the fluidic devices 360 to collect fluid from and deposit fluid into the fluidic devices 360. The movement system 310 includes a z-axis actuator 312 that is coupled to and moves the fluid collection device 320 along the z-axis. Unlike the movement system 110, however, the movement system 310 does not couple the fluid collection system 320 to x-axis and y-axis actuators. Instead, to provide relative movement between the fluid collection device 320 and the fluidic devices 360 along the x-axis and the y-axis, the movement system 310 moves the platform 350 along the x-axis and the y-axis.

In operation, the movement system 310 moves the platform 350 until an output port 362 or an input port 364 of a selected fluidic device 360 is aligned with the fluid collection device 320 along the x-axis and the y-axis. Once the proper relative positioning along the x-axis and the y-axis is achieved, the z-axis actuator 312 of the movement system 310 moves the fluid collection device 320 along the z-axis so that the tip 322 can engage the output port 362 or the input port 364. The movement system 320 can move any of the fluidic devices 360 relative to the fluid collection device 320 to execute any protocol of fluid transfers with the fluidic devices 360.

As shown in FIGS. 3 and 4, one or more storage components 330 for banking the tips 322 can also be disposed on the platform 350. The platform 350 can also include connections (e.g., tubing) to analysis instruments that allow collected fluid to be deposited for analysis by the instruments. Although the movement system 310 may operate differently to position the fluidic devices 360 relative to the fluid collection device 320, the system 300 can operate substantially in the same manner as the system 100 described above. As described above, for example, two or more fluid collection devices 320 can be coupled to the z-axis actuator 312 to allow simultaneous processing of two or more fluidic devices 360, e.g., using the same or similar protocol.

Figure 5:
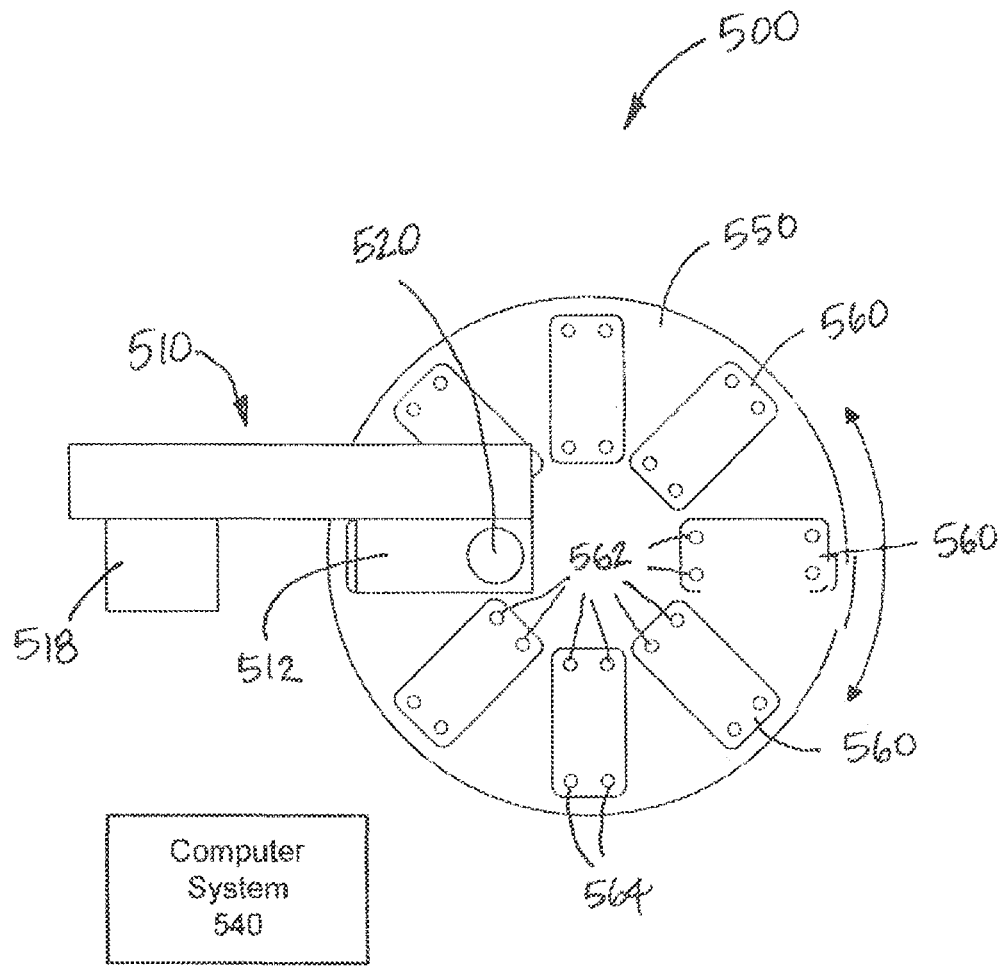
FIG. 5 illustrates yet another example interconnection system for a plurality of fluidic devices according to aspects of the present invention.

Referring to FIG. 5, yet another example interconnection system 500 according to aspects of the present invention is illustrated. The system 500 is also similar in many aspects to the system 100 shown in FIGS. 1 and 2. The system 500 includes a movement system 510, a fluid collection device 520, and one or more fluidic devices 560 arranged on a platform 550. A computer system 540 controls aspects of the system 500. The fluidic devices 560 may be fluidic and/or microfluidic. Each fluidic device 560 includes an output port 562 though which fluid can be collected from the fluidic device 560 and an input port 564 through which fluid can be deposited into the fluidic device 560. The fluid collection device 520 includes a tip 522 that engages the output port 562 or the input port 564 of a selected fluidic device 560 to collect or deposit fluid, respectively. The movement system 510 causes relative movement between the fluid collection device 520 and the fluidic devices 560 to collect fluid from and deposit fluid into the fluidic devices 560. The movement system 510 includes a z-axis actuator 512 and an x-axis actuator 514 that are coupled to and move the fluid collection device 520 linearly along the z-axis and the x-axis, respectively. Unlike the movement system 110, however, the movement system 510 does not couple the fluid collection system 520 to a y-axis actuator. Instead, to provide relative movement between the fluid collection device 520 and the fluidic devices 360 along the y-axis, the movement system 510 rotates the platform 550 about the z-axis.

In operation, the platform 550 rotates a selected fluidic device 560 into alignment with the fluid collection device 520 along the y-axis, and the x-axis actuator 514 moves the selected fluidic device 560 linearly into alignment with the fluid collection device 520. Once the proper relative positioning along the x-axis and the y-axis is achieved, the z-axis actuator 512 moves the fluid collection device 520 along the z-axis so that the tip 522 can engage the output port 562 or the input port 564. The movement system 520 can move any of the fluidic devices 560 relative to the fluid collection device 520 to execute any fluid transfer protocol with the fluidic devices 560. Although the movement system 510 may operate differently to position the fluidic devices 560 relative to the fluid collection device 520, the system 500 can operate substantially in the same manner as the systems 100 and 300 described above.

The fluidic devices 560 may be arranged in any configuration on the rotary table. As shown in FIG. 5, the fluidic devices 560 are aligned radially on the platform 550. As such, the platform 550 can be rotated to at selected speeds to subject the contents of the fluidic devices 560 to centrifugal forces to simulate gravity or other forces.

Figure 6:
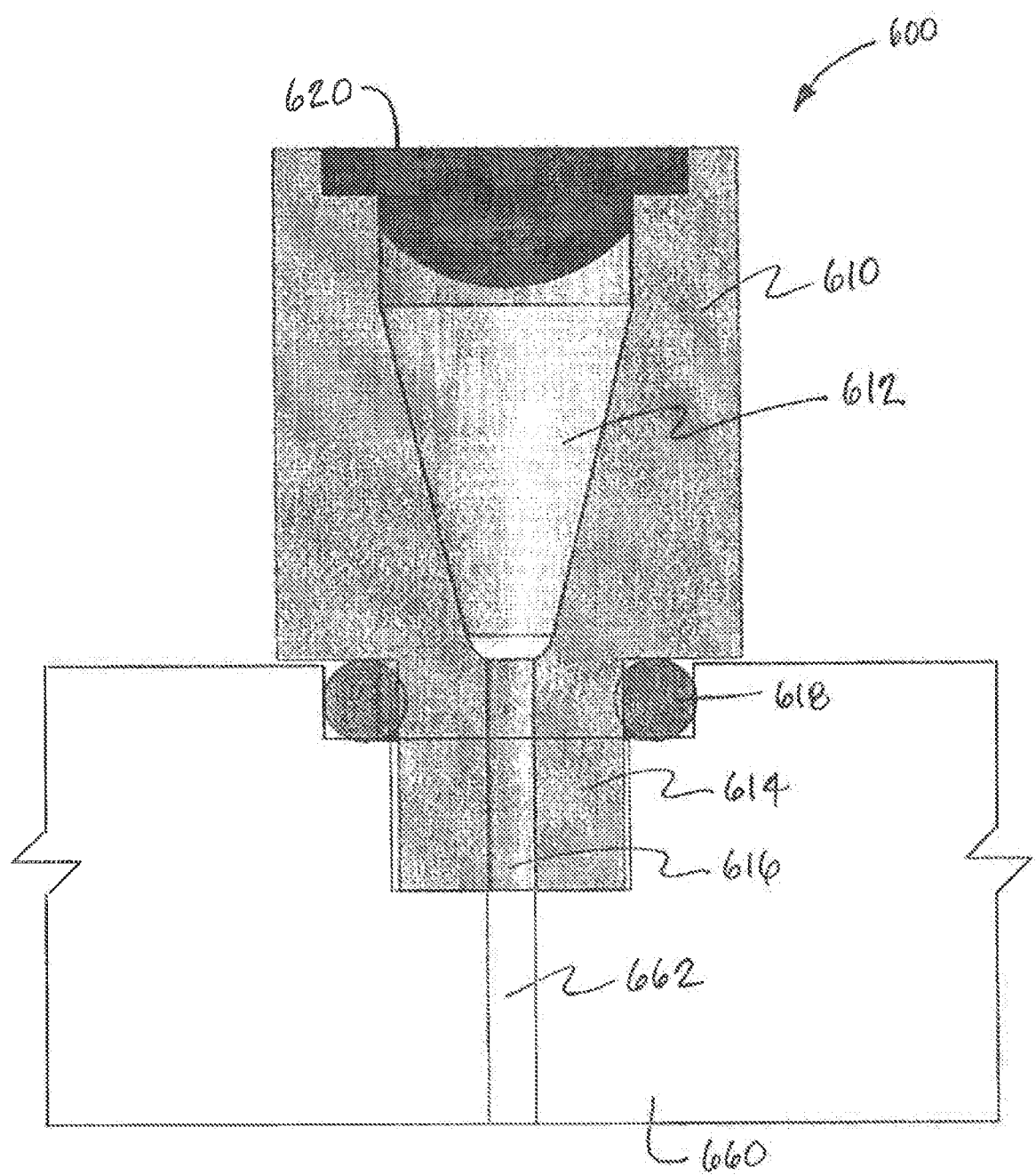
FIG. 6 illustrates an example port structure for a fluidic device with a sealing septum to cover a chamber of the port structure according to aspects of the present invention.

According to aspects of the present invention, chambers may be defined for the output ports and the input ports and the fluid collection device accesses these chambers, e.g., with a tip, to collect fluid from the output ports or deposit fluid into the input ports. The chambers for the output ports receive fluid from an output channel of the fluidic device for collection by the fluid collection device. Meanwhile, the chambers of the input ports receive fluid from the fluid collection device for deposit in an input channel of the fluidic device. While some embodiments permit the chambers to remain uncovered, uncovered chambers pose the risk of contamination as well as fluid loss through evaporation. Referring to FIG. 6, an example port structure 600 according to aspects of the present invention is illustrated. The port structure 600 includes a port body 610 that provides a sealed chamber 612 for an output port or an input port. The port structure 600 can be employed on a fluidic device 660 as described above. As shown in FIG. 6, the port structure 600 includes a nozzle 614 that can be inserted into a recess in the top surface of the fluidic device 660. The nozzle 614 can be coupled to the fluidic device 660 by a threaded connection, a press-fit or snap-fit connection, adhesive, heat-staking, welding, or any other appropriate technique. A seal 618, such as an O-ring, can also be provided for the coupling. The nozzle 614 includes a channel 616 that connects the chamber 612 with an input or output channel 662 of the fluidic device 660. In some cases, the chamber 612 is conical in shape and narrows as it extends toward the channel 616, in part to cause all the fluid to drain into the fluidic device 660. The top of the port body 610 includes a sealing septum 620 that prevents contaminants from entering the chamber 612 and minimizes evaporation of the fluid contained in the chamber 612. In other embodiments, the fluidic device 600 can be adapted to form a port structure 600.

In some embodiments, the sealing septum 620 is initially solid across the chamber 612 and a sharp, e.g., needle-like, tip on the fluid collection device is required to pierce the sealing septum 620 and gain access to the chamber 612. Once pierced, the sealing septum 620 may or may not re-seal. Although the sealing septum 620 shown in FIG. 6 appears to be substantially planar, it is understood that other embodiments may use a sealing septum 620 that are more concave or convex in shape.

Figure 7:
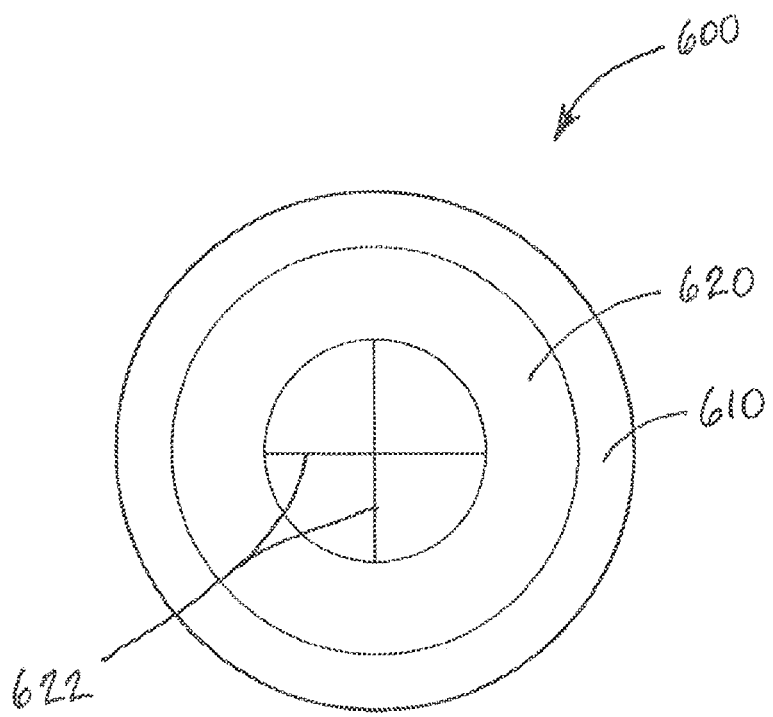
FIG. 7 illustrates an example sealing septum to cover a chamber of a port structure for a fluidic device according to aspects of the present invention.

Alternatively, as shown in FIG. 7, the sealing septum 620 may include one or more pre-formed slits 622 that enable the tip of the fluid collection device 120, 320, 520 to be inserted into the chamber 612 to collect or deposit fluid without requiring a piercing step. The sealing septum 620 can be sufficiently resilient to return to its original shape to seal the chamber 612 when the tip is removed. In some cases, the sealing septum 620 is formed from a material, such as PDMS, Silicone, Rubber, Latex, styrene-ethylene/butylene-styrene (SEBS), polyurethane, PTFE, FKM, FFKM or other fluoroelastomers. In other cases, the sealing septum 620 can be formed from a laminate of multiple materials, not all of which are elastomers. For example, the sealing septum 620 can include a combination of aluminum-foil laminated to silicone. Although the slits sealing septum 622 shown in FIG. 7 may include two slits 622 that intersect to form a cross, it is understood that other embodiments may employ any number of slits 622 that form other shapes.

Although the embodiments shown in FIGS. 6 and 7 employ a sealing septum 620 to cover the chamber 612, other embodiments may employ other structures that provide an equally protective cover for the chamber. For example, an alternative structure similar to a duckbill valve may be employed to cover the chamber. Similar to the sealing septum, this alternative structure is formed from elastomeric material with a pre-formed opening that functions to re-seal the chamber.

Instead of, or in addition to, using an elastomeric cover such the sealing septum 612 described above, other embodiments cover the chamber with other types of structure. For example, the port body 610 can include a valve, such as a gate, ball or globe valve, that can be opened to allow the tip to be inserted into the chamber 612 and closed after the tip is removed.

Figure 8:
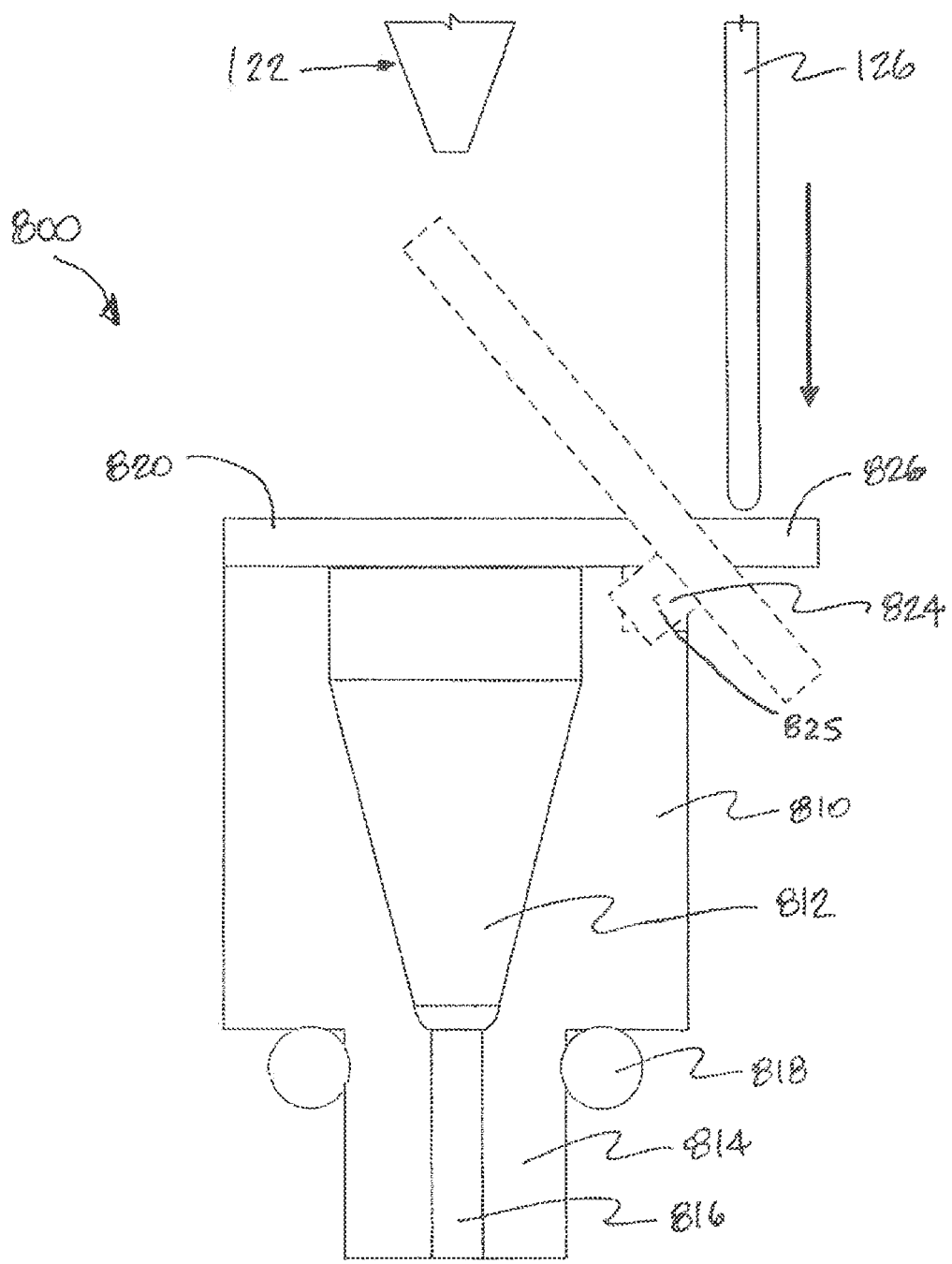
FIG. 8 illustrates an example movable cover for the chamber of a fluidic device according to aspects of the present invention.

In other embodiments, the chamber is covered with an actuated movable cover. The movable cover operates to open an access to the chamber so that the tip of a fluid collection device can be inserted into the chamber to collect or deposit fluid. After collection or deposit, the movable cover operates to close the access to the chamber to prevent contamination and to minimize evaporation. Referring to FIG. 8, an example moveable cover according to aspects of the present invention is illustrated. Like the port structure 600 shown in FIG. 6, the port structure 800 can includes a chamber 812 that can be coupled to a fluidic device. A seal 818, such as an O-ring, can also be provided for the coupling. The nozzle 814 includes a channel 816 that connects the chamber 812 with an input or output channel of the fluidic device. The port 820 includes a movable cover 820 with a substantially planar or curved lower surface that can sit against the upper surface of the port body 810 to cover the opening to the chamber 812. A pivoting arm 824 extends from the movable cover 820 and pivots about a pin 825 that is supported by the port body 810. The pivoting arm 824 includes a tab 826 that extends away from the movable cover 820, on the other side of the pin 825.

The fluid collection device 120 as shown in FIG. 8 includes a pushrod 126 that extends past the tip 122 of the fluid collection device 120. In operation, when the tip 122 of the fluid collection device 120 moves downwardly toward the chamber 812, the pushrod 126 moves with the fluid collection device 120 to push against the tab 826. The tab 826 also moves correspondingly in the same direction, e.g., downwardly, and causes the pivoting arm 824 to pivot about the pin 825. Because the movable cover 820 is on the other side of the pin 825, the movable cover 820 moves in the opposite direction, e.g., upwardly, to uncover the chamber 812 and allow the tip 122 to access the chamber 812. The pushrod 126 extends from the fluid collection device 120 with a length that is sufficient to allow the movable cover 820 to uncover the chamber 812 without interference from the tip 122 as the tip 122 moves toward the chamber 812. The pivoting arm 824 may be biased, e.g., by a spring or gravity, to act against this motion of the movable cover 820. In a default state, the bias positions the movable cover 820 against the top of the chamber 812 to keep the chamber 812 covered. As such, the pushrod 126 must maintain contact with the tab 826 to keep the chamber 812 uncovered. As the tip 122 is removed upwardly from the chamber 812, the pushrod 126 moves in the same direction. The bias of the pivoting arm 824 causes the tab 826 to move with the pushrod 126 and the movable cover 820 to move in the opposite direction and cover the chamber 812. The top surface of the port body 810 or the bottom surface of the moveable cover 820 may include a sealing element, such as an O-ring or a resilient material that can provide improved sealing properties when the moveable cover 820 sits over the chamber 812. In other embodiments, the pushrod 126 can involve a flexible element, which can simplify the geometric considerations in the design. Alternatively, the pushrod 126 can be replaced with or supplemented with a controlled actuator that is coupled to the fluid collection device 120, for example, a pneumatic piston, solenoid, electromechanical linear actuator, magnet, and/or electromagnet.

Figure 11:
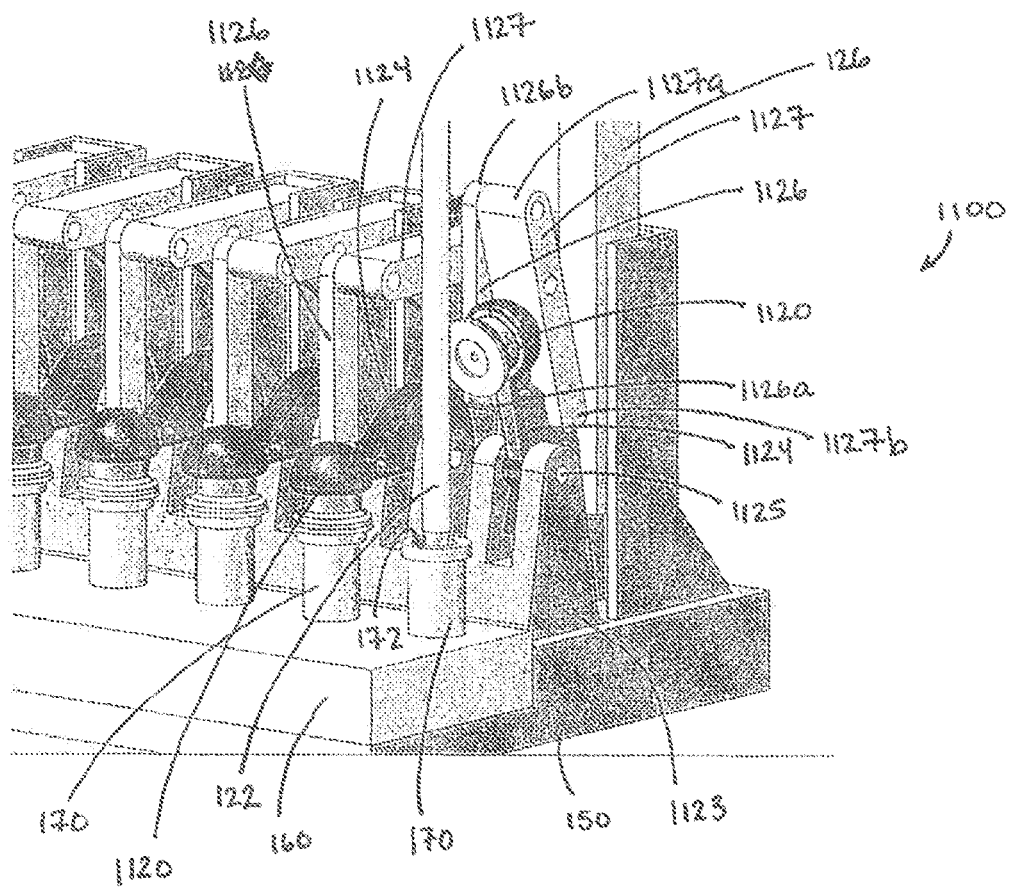
FIG. 11 illustrates another example movable cover for the chamber of a fluidic device according to aspects of the present invention.

Referring to FIG. 11, another example movable cover according to aspects of the present invention is illustrated. The movable covers 1120 are implemented on a cover system 1100 disposed on the platform 150 on which the fluidic devices 160 are arranged. As shown in FIG. 11, the movable covers 1120 cover the chambers 172 of port structures 170 disposed on fluidic devices 160. The port structures 170 may be similar to the port structures described above. Each movable cover 1120 is coupled to a pivoting arm 1124 that pivots about a first pin 1125 supported by a base 1123 extending upwardly from the platform 1150. In its default state, a bias, e.g., from a spring or gravity, causes the pivoting arm 1124 to hold the movable cover 1120 against the top of the chamber 172 to keep the chamber 172 covered. A first end 1126a of a first linkage arm 1126 is coupled to the pivoting arm 1124 and extends upwardly to a second linkage arm 1127 where a second end 1126b of the first linkage arm 1126 is coupled a first end 1127a of the second linkage arm 1127. The second linkage arm 1127 pivots about a second pin 1128 that is supported by a vertical structure 1129 that also extends upwardly from the platform 150. The bias applies a downward force on the first linkage arm 1126 and the first end 1127a of the second linkage arm 1127b, which in turn causes the second linkage arm 1127b to maintain a substantially horizontal orientation.

The fluid collection 120 device includes a pushrod 126 as shown in FIG. 11 that extends downwardly with the tip 122 of the fluid collection device 120. In operation, when the tip 122 of the fluid collection device 120 moves downwardly toward the chamber 172, the pushrod 126 moves with the fluid collection device 120 to push downwardly against a second end 1127b of the second linkage arm 1127. This causes the second linkage arm 1127 to pivot about the second pin 1128 and the first end 1127a of the second linkage arm 1127 to move upwardly. Because the first linkage arm 1126 is coupled to the first end 1127a of the second linkage arm 1127, the first linkage arm 1126 also moves upwardly. The upward movement of the first linkage arm 1126 pulls the moveably cover 1120 upward to pivot about the first pin 1125 against the bias and to uncover the chamber 172, which allows the tip 122 to access the chamber 172. As the tip 122 is moved upwardly, from the chamber 172, the pushrod 126 also moves upwardly. The bias of the pivoting arm 1124 causes the second end 1127b of the second linkage arm 1127 to move upwardly with the pushrod 126. As the second linkage arm 1127 pivots, the first end 1127a of the second linkage arm 1127 moves downwardly allowing the first linkage arm 1126 to also move downwardly. This in turn allows the movable cover 1120 to move against the top of the chamber 172 and to cover the chamber 172.

Accordingly, the embodiments shown in FIGS. 8 and 11 provide a moveable cover for covering the chamber of a fluidic device can be supported by the fluidic device itself (FIG. 8) or may be supported by some other structure in the interconnection system (FIG. 11). While the movable cover in the embodiments of FIGS. 8 and 11 may operate in response to a push rod 126 or other mechanism that moves with the fluid collection device 120, it is understood that other techniques for actuating movement of a movable cover may be employed. For example, the movable cover may be actuated by mechanical, electromechanical, magnetic, pneumatic (or vacuum), electrical, piezoelectric, or other similar mechanisms. In general, an actuated movable cover of any appropriate structure may be employed to selectively uncover the chamber in a port of a fluidic device for fluid collection or deposit.

In interconnection systems where 1 microliter, 2 microliters, 3 microliters, 4 microliters, 5 microliters, 10 microliters, 20 microliters, 30 microliters, 40 microliters, 50 microliters, and volumes up to 5 milliliters are to be transferred, such small volumes can be significantly impacted by evaporation. In particular, evaporation can result in significant changes in the concentrations of constituent components. By minimizing evaporation and maintaining the integrity of the fluids in fluidic devices, mechanisms, such as a sealing septum or an actuated movable cover, make it feasible for an interconnection system to process relatively small volumes of fluid.

In some embodiments, it may also be desirable to provide venting to accommodate changes in air pressure as fluid is collected from or deposited into covered chambers. The port structures 600 shown in FIG. 6, for example, can be configured to handle changes in air pressure in a covered chamber 612, 812. In particular, at an input port 614, a negative pressure is generated in the covered chamber 612 as fluid is drawn from the chamber 612 into the fluidic device 660. Conversely, at an output port 612, as fluid is introduced into the covered chamber 612 from the fluidic device 660, a positive pressure is generated in the chamber 612. According to aspects of the present invention, the port body 610 or the sealing septum 620 can deform to accommodate the changes in internal pressure in the chamber 612 until access to the chamber 612 is opened more fully and the pressure equalizes. Additionally or alternatively, one or more slits 622 in the sealing septum 620 can allow air to vent into or out of the chamber 612. Additionally or alternatively, the port structure 600 can include one or more small and/or deep vent holes. Additionally or alternatively, a separate gas permeable section can be provided in (or coupled to) the port structure 600 to relieve pressure in the chamber 612. In some cases, the gas permeable section can be sized to limit evaporation as much as possible. In other cases, the gas permeable section includes a membrane that is permeable to gas, but not water vapor, to minimize the impact of evaporation. An example of a gas permeable membrane is disclosed in PCT Application No. PCT/US2012/068725, filed Dec. 10, 2012 and U.S. Provisional Application No. 61/696, 997, filed on Sep. 5, 2012 and No. 61/735,215, filed on Dec. 10, 2012, the contents of each application is incorporated herein by reference in its entirety.

According to aspects of the present invention, the fluidic devices can be connected to one or more valves that enable fluids to be deposited into the input ports or collected from the output ports. For example, some fluidic devices can receive a steady or substantially steady flow of fresh media into one or more of the device's channels. Instead of using the fluid collection device to continuously supply the input port with fresh media, a selector valve can be coupled to the input port to selectively supply fresh media to the fluidic device, e.g., via a tube connected to a media source. Similarly, some fluidic devices can produce a steady or substantially steady flow of waste fluid. Instead of using the fluidic collection device to continuously remove waste fluid through the output port, a selector valve can be coupled to the output port to selectively draw the waste fluid out to a waste collection reservoir, e.g., via tubing.

In some embodiments, a selector valve can be used to couple the input port to several different sources of media, e.g., media that can contain different drugs or pathogens. Additionally, a selector valve can be used to couple the output port to several different outputs, e.g., various collection reservoirs that correspond to different time-points in an experiment. Valves can also be used to couple the input port and/or output port to a port structure that includes a chamber for transferring fluid as discussed above.

Figure 9:
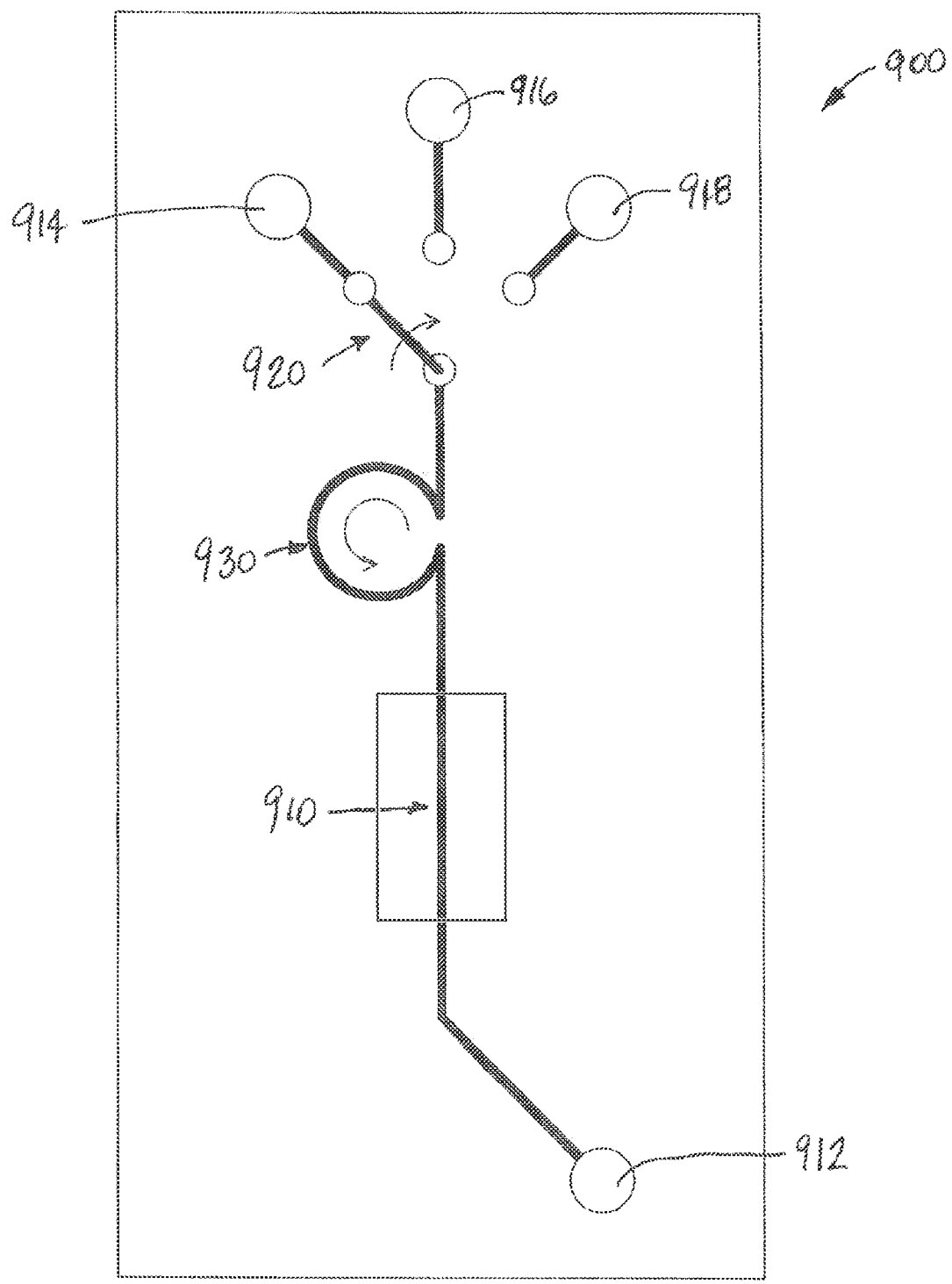
FIG. 9 illustrates an example microfluidic device according to aspects of the present invention.

Referring to FIG. 9, an example microfluidic device 900 according to aspects of the present invention is illustrated. The microfluidic device 900 can include one or more output ports 912 and one or more input ports 914, 916, 918, a selector switch 920, a pump 930, and a functionalized microfluidic channel 910. The functionalized microfluidic channel 910 may include one or more organ-chips including cells maintained in one or more microfluidic channels. According to aspects of the present invention, the selector switch 920 may be a motor-controlled switch that can control the source of the fluid input into the microfluidic device 900. For example, a first input port 914 can be coupled by tubing to a source of fresh media contained in an environmentally controlled reservoir. This fresh media can be used to maintain the viability of biologic material such as organ tissue in the microfluidic channel 910. The second input port 916 can be coupled to a port structure 600 to enable fluids from other sources to be input into the microfluidic channel 910 using the fluid collection device 120. The third input port 918 can be coupled by tubing to a source of media that includes a drug or a pathogen to be tested. The selector valve 920 can be used to connect one of the inputs to the microfluidic channel 910. The pump 930 can include a peristaltic pump that draws fluid from an input source and pumps it through the microfluidic channel 910 to the output port 912. The output port 912 can include a port structure 600 that includes a chamber 612 that holds the fluid until it can be withdrawn by a fluid collection device 120. The selector valve 930 can also include a position that seals the input of the microfluidic device 900, for example, to enable the microfluidic device to be transported without leaking or becoming contaminated.

According to aspects of the present invention, the output of the microfluidic component 910 can also be connected through a selector valve to more than one output. For example, one output can be connected to a waste container or by tubing to a storage reservoir. Another output can be connected to an output port structure 600 that enables the output fluid to be transferred by the fluid collection device 120 to instrumentation for analysis or to an input port of the same or another microfluidic device 900.

Figure 10:
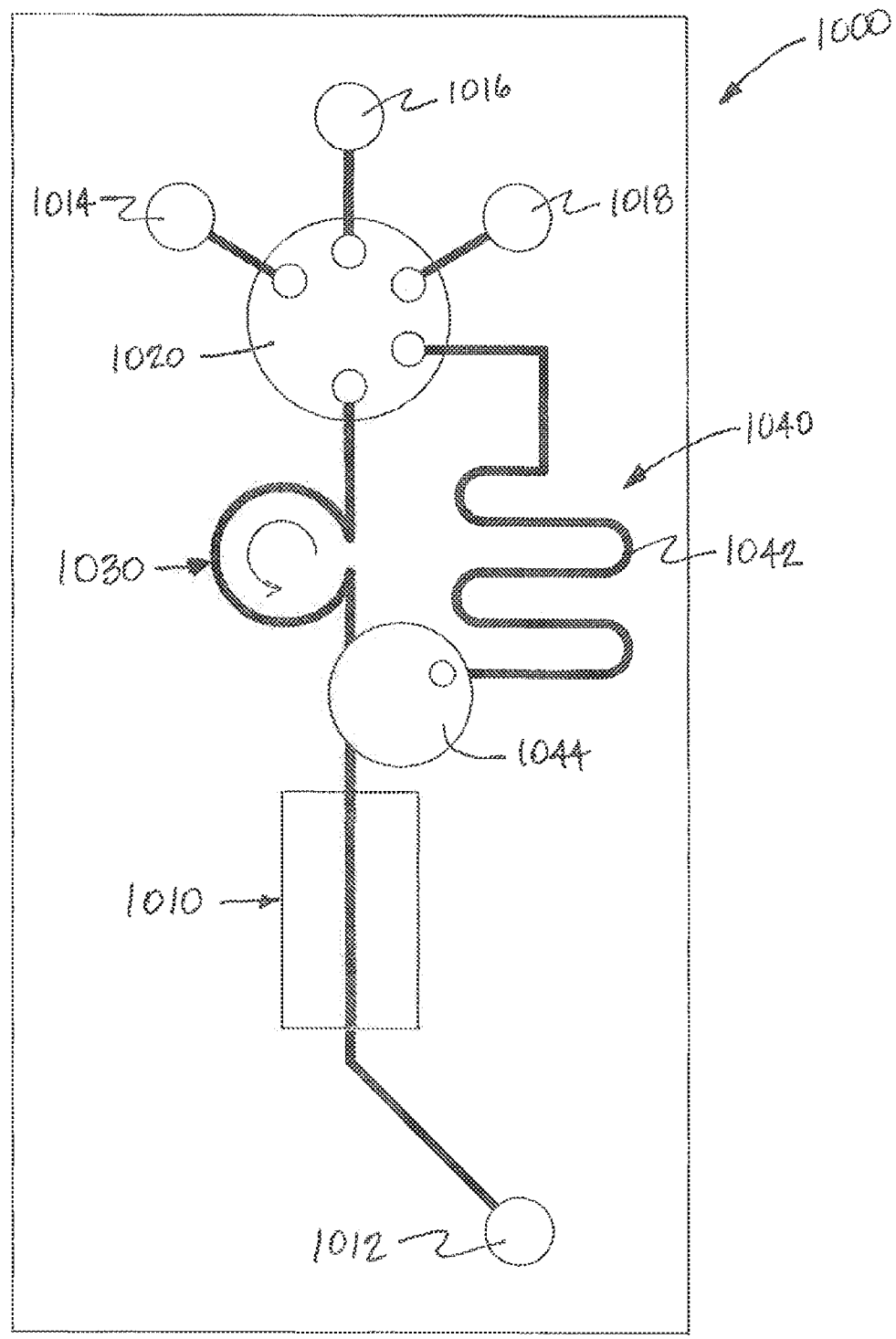
FIG. 10 illustrates another example microfluidic device according to aspects of the present invention.

Referring to FIG. 10, another example of a microfluidic device 1000 according to aspects of the present invention is illustrated. The microfluidic device 1000 can include one or more output ports 1012 and one or more input ports 1014, 1016, 1018, a selector valve 1020, a pump 1030, a fluid reservoir 1040 and a functionalized microfluidic component 1010. The functionalized microfluidic component 1010 can include one or more organ-chips including cells maintained in one or more microfluidic channels. Pump 1030 can include a peristaltic pump that draws fluid from an input source and pumps it through the microfluidic channel 1010 to the output port 1012. The output port 1012 can include a port structure 600 that includes a chamber 612 that holds the fluid until it can be withdrawn by a fluid collection device 120. The selector valve 1030 can also include a position that seals the input of the microfluidic device 1000, for example, to enable the microfluidic device to be transported without leaking or becoming contaminated.

According to aspects of the present invention, the selector switch 1020 can be a motor controlled switch that can be used to control the source of the fluid input into the device 1000. For example, a first input 1014 can be connected by tubing to a source of fresh media contained in an environmentally controlled reservoir. This fresh media can be used to maintain the viability of biologic material such as organ tissue in the microfluidic channel. The second input 1018 can be connected by tubing to a source of media that includes a drug or a pathogen to be tested. The third input 1016 can be connected to port structure 600 to enable fluids from other sources to be input into the microfluidic channel 1010. The fourth port can be a connection to the fluid reservoir 1040. The selector valve 1020 can be operated to connect one of the inputs to the microfluidic channel 1010. The selector valve 1020 can also be operated to connect the third input 1016 to the fluid reservoir 1040 in order to allow fluid deposited by the fluid collection device 120 to be stored locally in the fluid reservoir 1040 for later use. At a later time, the selector valve can be operated to connect the fluid reservoir 1040 to the microfluidic channel 1010 to input the stored fluid into the device 1000. According to aspects of the present invention, the fluid reservoir 1040 can include a vent to enable air to escape as it is being displaced by fluid being deposited into the fluid reservoir 1040. The vent can include a gas permeable membrane that allows air to escape as the reservoir 1040 is being filled and for air to return when fluid from the reservoir 1040 is pumped into the microfluidic channel 1010. According to aspects of the present invention, the microfluidic device 1000 can include a gas permeable membrane that serves as a bubble trap and a portion of the gas permeable member used in the bubble trap can be used to vent the fluid reservoir 1040. Examples of bubble traps and gas permeable membrane that can be used are disclosed in PCT Application No. PCT/US2012/068725, filed Dec. 10, 2012 and U.S. Provisional Application No. 61/696,997, filed on Sep. 5, 2012 and No. 61/735,215, filed on Dec. 10, 2012, the contents of each application is incorporated herein by reference in its entirety. One of the advantages of using the fluid reservoir 1040 is that the selector valve 1020 can act a seal to close the fluid reservoir until the fluid is to be delivered to the microfluidic channel 1010 and there is no need for a sealing septum or cover on the port 1016 to minimize evaporation or contamination.

According to aspects of the present invention, the selector valve 1020 can be a selector valve that includes an open/closed valve in the fluidic channels leading to the microfluidic chip 1010 and the on-board reservoir 1042. This allows any of the selector valve inputs to be routed directly to the microfluidic chip 1010 or to the on board reservoir 1042 and enables the fluidic channels connected to the microfluidic chip 1010 and the on-board reservoir 1042 to be closed to avoid inadvertent connections. In some embodiments of the invention, selector valve 1020 can include two selector valves connected in series. The first selector valve can select among the fluid inputs (such as 1014, 1016, and 1018 in FIG. 10) and connects the selected input to a second selector valve. This second selector valve can select among the fluid outputs and connects the selected input to the selected output, such as, the on-board reservoir 1042 or the microfluidic chip 1010.

According to aspects of the present invention, the fluid reservoir 1040 can be formed from an elongated channel that maintains the time course (e.g., the character over time) of the fluid as it was received from the source. In accordance with this embodiment, the fluid obtained from the source device can be withdrawn using a fluid collecting device 120 that includes an elongated or microfluidic channel that also maintains the time course of the fluid received. In accordance with this embodiment, the source device can include an elongated or microfluidic channel that also maintains the time course of the fluid received. In some embodiments of the fluid collecting device 120, the time course is backwards in the sense that the fluid portion adjacent received last will be delivered first and the fluid portion received first will be delivered last. By injecting the fluid through the third port 1016 into the fluid reservoir 1040, the time course of the fluid becomes reversed such that when the fluid is delivered to the microfluidic channel 1010, the fluid portion that was received first (from the source) is delivered first into the microfluidic channel 1010.

One of the benefits of using the fluidic reservoir 1040 having an elongated channel is that the fluid collecting device can deposit a fluid sample into the reservoir 1040 at a very high rate (a rate that due to high pressure or flow rate could damage the microfluidic device or the biologic material contained therein) and move on to the next operation or task. Separately, the fluid sample stored in the fluid reservoir 1040 can be pumped into the microfluidic device at predefined rate, for example, a rate that does not risk damage to the device or the biologic material and a rate the preserves the time course of the fluid.

One of the benefits of using the fluidic reservoir 1040 having an elongated channel that maintains the time course of the fluid sample is that fluidic reservoir 1040 can be used to deliver large volumes of fluid samples over a predefined period of time. In addition, the fluid sample can be "constructed" by combining smaller discrete fluid samples from several sources to create a continuous time delivery sequence without requiring many consecutive fluid transfer events. This can provide for more effective scheduling of fluid transfer events. In accordance with some embodiments two or more fluidic reservoirs 1040 can be provided so that while one reservoir is being used to supply the system with fluid, an unused reservoir 1040 can be filled with the next course of fluid.

As described above, the cell culture devices can be used to mimic aspects of a biological cell system, e.g., a tissue type or organ. Such cell culture devices are also referred to organ-chips. The organ-chips can be configured to mimic the functionality of any living organ from humans or other organisms (e.g., animals, insects, plants). As such, the systems, devices, and instruments described herein can be used to model or study mammalian as well as non-mammalian (e.g., insects, plants, etc.) organs and physiological systems and effect of active agents on such organs and physiological systems.

Examples of organ-chips that can be used in the methods and systems according to the invention include, for example, in U.S. Provisional Application No. 61/470,987, filed Apr. 1, 2011; No. 61/492,609, filed Jun. 2, 2011; No. 61/447,540, filed Feb. 28, 2011; No. 61/449,925, filed Mar. 7, 2011; and No. 61/569,029, filed on Dec. 9, 2011, in U.S. patent application Ser. No. 13/054,095, filed Jul. 16, 2008, and in International Application No. PCT/US2009/050830, filed Jul. 16, 2009 and PCT/US2010/021195, filed Jan. 15, 2010, the contents of each application is incorporated herein by reference in its entirety. Muscle organ-chips are described, for example, in U.S. Provisional Patent Application Ser. No. 61/569,028, filed on Dec. 9, 2011, U.S. Provisional Patent Application Ser. No. 61/697,121, filed on Sep. 5, 2012, and PCT patent application titled "Muscle Chips and Methods of Use Thereof," filed on Dec. 10, 2012 and which claims priority to the U.S. provisional application No. 61/569,028, filed on Dec. 9, 2011, U.S. Provisional Patent Application Ser. No. 61/697,121, the contents of each application is incorporated herein by reference in its entirety.

The organ-chips can also include control ports for application of mechanical modulation (e.g., side chambers to apply cyclic vacuum, as in the Lung Chip described in the PCT Application No.: PCT/US2009/050830) and electrical connections (e.g., for electrophysiological analysis of muscle and nerve conduction). A similar approach of producing the Lung Chips with or without aerosol delivery capabilities (which can be extended to produce other organ-chips, e.g., heart chips and liver chips) is described, e.g., in the PCT Application No.: PCT/US2009/050830 and U.S. Provisional Application Nos. 61/483,837 and 61/541,876, the contents of each application is incorporated herein by reference in its entirety.

In accordance with embodiments of the invention, the microfluidic device (e.g., which can include a cartridge) can include a base substrate. The base substrate can provide: (a) a holder and/or microfluidic connections for at least one organ-chip; and (b) at least one fluidic circuit having an input port and an output port, in connection with at least one organ-chip (or other device having fluidic or microfluidic components), wherein the fluidic circuit can allows fluid communication between the organ-chip (or other device having fluidic or microfluidic components) attached to the cartridge and other components of the microfluidic system. Exemplary cartridges are described in, for example, PCT Application No. PCT/US2012/068725, filed Dec. 10, 2012 and U.S. Provisional Application No. 61/696,997, filed on Sep. 5, 2012 and No. 61/735,215, filed on Dec. 10, 2012, contents of each application is incorporated herein by reference in its entirety.

For purposes of illustration, aspects of the present invention are described in the context of diagrammatic examples of fluidic interconnection systems according to embodiments of the invention. As used herein the terms fluidic and microfluidic, unless the context clearly indicated otherwise, are used interchangeably. While the invention may, in some circumstances, be better suited for use with microfluidic devices and systems, the invention may, in some circumstances, also be better suited for use with fluidic devices and systems.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein.

What is claimed is:

1. A method for facilitating biological communication between two or more microfluidic cell culture devices by transferring fluid from a first microfluidic cell culture device to a second microfluidic cell culture device, the method comprising:

providing a system comprising (a) the first microfluidic cell culture device having an output port, (b) the second microfluidic cell culture device having an input port, (c) a fluid collection device coupled to a movement system that is configured to move the fluid collection device into a desired position relative to at least one of the first cell culture device and the second cell culture device, and (d) a perfusion mechanism, moving the fluid collection device to a first desired position relative to the first microfluidic cell culture device comprising a microfluidic channel including a first organ tissue;

collecting a first discrete fluid volume from said output port of the first microfluidic cell culture device;

moving the fluid collection device to a second desired position relative to the second microfluidic cell culture device comprising a microfluidic channel including a second organ tissue;

depositing a second discrete fluid volume comprising at least a portion of the first discrete fluid volume into said input port of the second microfluidic cell culture device; and perfusing, using said perfusion mechanism, the respective second discrete fluid volume through the second microfluidic cell culture device.

2. The method according to claim 1 wherein the first microfluidic cell culture device or the second microfluidic cell culture device includes a chamber configured to hold correspondingly the respective first discrete fluid volume or the respective second discrete fluid volume, the desired position is determined according to the chamber, and the fluid collection device correspondingly collects the respective first discrete fluid volume from or deposits the respective second discrete fluid volume into the chamber.

3. The method according to claim 1 wherein the output port includes a port structure, the port structure including a chamber for receiving the respective first discrete fluid volume to be collected by the fluid collection device.

4. The method according to claim 1 wherein the input port includes a port structure, the port structure including a chamber for receiving the respective second discrete fluid volume from the fluid collection device.

5. The method according to claim 1 wherein the output port or the input port includes a port structure, the port structure including a chamber for storing fluid that is to be collected by the fluid collection device or that is received from the fluid collection device, the chamber being covered to minimize contamination and fluid evaporation in the chamber.

6. The method according to claim 1 wherein the fluid collection device includes a collection chamber selected from the group consisting of an elongated chamber, capillary channel, or a microfluidic channel that receives a plurality of samples of fluid over a period of time, each sample of fluid substantially maintaining at least one physical, chemical, or biochemical characteristic from a time the sample was collected, the plurality of samples providing time-based information regarding the at least one physical, chemical, or biochemical characteristic.

7. The method according to claim 1 further comprising:
moving the fluid collection device to a third desired position relative to a third microfluidic cell culture device; and depositing a third discrete fluid volume into a port of the third microfluidic cell culture device, wherein the third discrete fluid volume includes at least another portion of the first discrete fluid volume collected from the first microfluidic cell culture device.

* * * * *